(12) United States Patent
Badruddin et al.

(10) Patent No.: US 11,185,335 B2
(45) Date of Patent: Nov. 30, 2021

(54) SYSTEM FOR AND METHOD OF TREATING ANEURYSMS

(71) Applicant: Galaxy Therapeutics Inc., Milpitas, CA (US)

(72) Inventors: Aamir Badruddin, Bolingbrook, IL (US); Edgard Luiz Ramos Pereira, Boca Raton, FL (US); Thomas J. Wolfe, Shorewood, WI (US); Osama O. Zaidat, Lambertville, MI (US)

(73) Assignee: Galaxy Therapeutics Inc., Milpitas, CA (US)

( * ) Notice: Subject to any disclaimer, the term of this patent is extended or adjusted under 35 U.S.C. 154(b) by 0 days.

(21) Appl. No.: 15/875,767

(22) Filed: Jan. 19, 2018

(65) Prior Publication Data
US 2019/0223876 A1 Jul. 25, 2019

(51) Int. Cl.
A61B 17/12 (2006.01)
A61B 90/00 (2016.01)
A61F 2/82 (2013.01)

(52) U.S. Cl.
CPC .... A61B 17/1214 (2013.01); A61B 17/12031 (2013.01); A61B 17/12113 (2013.01);
(Continued)

(58) Field of Classification Search
CPC ........ A61B 17/12159; A61B 17/12163; A61B 2017/1205; A61B 2017/12054;
(Continued)

(56) References Cited

U.S. PATENT DOCUMENTS 6,506,204 B2 1/2003 Mazzochi
6,936,055 B1 8/2005 Ken et al.
(Continued)

FOREIGN PATENT DOCUMENTS

DE 102012016555 A1 2/2014
DE 102013006503 A1 7/2014
(Continued)

OTHER PUBLICATIONS http://www.asianjns.org/articles/2012/7/4/images/AsianJNeurosurg_2012_7_4_159_106643_f7.jpg, Available at least as early as Jul. 20, 2017.
(Continued)

Primary Examiner — Katherine H Schwiker
(74) Attorney, Agent, or Firm — Blair Walker IP Services, LLC

(57) ABSTRACT

An apparatus for treating an aneurysm in a blood vessel includes an occlusion element disposed on a wire, the occlusion element including a cover for covering a neck of an aneurysm and an inner anchoring member. The cover is configured to expand from a compressed configuration in a tube to an expanded configuration when advanced out of a distal end of the tube to cover the neck of the aneurysm. The cover includes a sphere of mesh material formed into a hemisphere including two layers of mesh that is formed by folding a top portion of the sphere into a bottom portion of the sphere. The inner anchoring member is coupled to and extends from the second surface of the cover and is configured to contact an interior surface of the aneurysm. The inner anchoring member may be a cylindrical stem extending from a central portion of the cover.

9 Claims, 16 Drawing Sheets

(52) U.S. Cl.
CPC .. *A61B 17/12118* (2013.01); *A61B 17/12172* (2013.01); *A61B 17/12177* (2013.01); *A61B 17/12145* (2013.01); *A61B 2017/1205* (2013.01); *A61B 2090/0807* (2016.02); *A61F 2002/823* (2013.01)

(58) Field of Classification Search
CPC ........... A61B 2017/12095; A61B 2017/00632; A61B 2017/00575; A61B 2017/00592; A61B 2017/00601; A61B 2017/00606; A61B 2017/0061; A61B 2017/00615; A61B 17/12022; A61B 17/12031; A61B 17/12036; A61B 17/12109; A61B 17/12113; A61B 17/12118; A61B 17/1214; A61B 17/12145; A61B 17/1215; A61B 17/12168; A61B 17/12172; A61B 17/12177; A61B 17/12122; A61F 2/01; A61F 2002/016; A61F 2002/018; A61F 2002/011

See application file for complete search history.

(56) References Cited

U.S. PATENT DOCUMENTS

| | | | |
|---|---|---|---|
| 7,128,736 B1 | 10/2006 | Abrams et al. | |
| 7,195,636 B2 | 3/2007 | Avellanet et al. | |
| 7,229,461 B2 | 6/2007 | Chin et al. | |
| 7,569,066 B2 | 8/2009 | Gerberding et al. | |
| 8,398,670 B2 | 3/2013 | Amplatz et al. | |
| 8,551,132 B2 | 10/2013 | Eskridge et al. | |
| 8,597,320 B2 | 12/2013 | Sepetka et al. | |
| 8,820,207 B2 | 9/2014 | Marchand et al. | |
| 8,826,791 B2 | 9/2014 | Thompson et al. | |
| 9,107,670 B2 | 8/2015 | Hannes et al. | |
| 9,198,668 B2 | 12/2015 | Theobald et al. | |
| 9,259,337 B2 | 2/2016 | Cox et al. | |
| 9,585,670 B2 | 3/2017 | Hines | |
| 9,597,087 B2 | 3/2017 | Marchand et al. | |
| 9,629,635 B2 | 4/2017 | Hewitt et al. | |
| 9,918,720 B2 | 3/2018 | Marchand et al. | |
| 2003/0195553 A1* | 10/2003 | Wallace | A61B 17/12022 606/200 |
| 2004/0034386 A1 | 2/2004 | Fulton et al. | |
| 2004/0044391 A1 | 3/2004 | Porter | |
| 2005/0033409 A1 | 2/2005 | Burke et al. | |
| 2005/0277978 A1 | 12/2005 | Greenhalgh | |
| 2006/0064151 A1 | 3/2006 | Guterman et al. | |
| 2006/0167494 A1* | 7/2006 | Suddaby | A61B 17/12022 606/213 |
| 2007/0173928 A1 | 7/2007 | Morsi | |
| 2007/0225794 A1 | 9/2007 | Thramann et al. | |
| 2007/0270902 A1 | 11/2007 | Slazas et al. | |
| 2008/0097495 A1* | 4/2008 | Feller, III | A61B 17/12022 606/157 |
| 2008/0147100 A1 | 6/2008 | Wallace | |
| 2008/0281350 A1 | 11/2008 | Sepetka et al. | |
| 2008/0319533 A1 | 12/2008 | Lehe | |
| 2009/0062841 A1* | 3/2009 | Amplatz | A61B 17/12022 606/200 |
| 2009/0082803 A1 | 3/2009 | Adams et al. | |
| 2009/0099647 A1 | 4/2009 | Glimsdale et al. | |
| 2009/0264978 A1 | 10/2009 | Dieck et al. | |
| 2009/0287291 A1 | 11/2009 | Becking et al. | |
| 2009/0318941 A1 | 12/2009 | Sepetka et al. | |
| 2011/0046719 A1* | 2/2011 | Frid | A61B 17/12022 623/1.18 |
| 2011/0202085 A1 | 8/2011 | Loganathan et al. | |
| 2012/0065667 A1* | 3/2012 | Javois | A61B 17/12122 606/213 |
| 2012/0143317 A1 | 6/2012 | Cam et al. | |
| 2012/0283768 A1 | 11/2012 | Cox et al. | |
| 2012/0303052 A1* | 11/2012 | Connor | A61B 17/12113 606/194 |
| 2012/0330347 A1 | 12/2012 | Becking et al. | |
| 2013/0035712 A1* | 2/2013 | Theobald | A61B 17/12172 606/198 |
| 2013/0066357 A1* | 3/2013 | Aboytes | A61M 29/02 606/198 |
| 2013/0073026 A1 | 3/2013 | Russo et al. | |
| 2013/0190800 A1 | 7/2013 | Murphy et al. | |
| 2013/0211495 A1 | 8/2013 | Halden et al. | |
| 2013/0325053 A1 | 12/2013 | Porter et al. | |
| 2014/0005714 A1 | 1/2014 | Quick et al. | |
| 2014/0012303 A1 | 1/2014 | Heipl | |
| 2014/0172001 A1 | 6/2014 | Becking et al. | |
| 2014/0257360 A1 | 9/2014 | Keillor | |
| 2014/0343602 A1 | 11/2014 | Cox et al. | |
| 2015/0005811 A1 | 1/2015 | Lubock et al. | |
| 2015/0133989 A1 | 5/2015 | Lubock et al. | |
| 2015/0250628 A1 | 9/2015 | Monstadt et al. | |
| 2015/0272589 A1 | 10/2015 | Lorenzo | |
| 2015/0313605 A1* | 11/2015 | Griffin | A61B 17/12 606/200 |
| 2016/0022445 A1* | 1/2016 | Ruvalcaba | A61B 17/12113 606/198 |
| 2016/0030050 A1 | 2/2016 | Franano et al. | |
| 2016/0278749 A1* | 9/2016 | Javois | A61B 17/12122 |
| 2017/0014114 A1* | 1/2017 | Rafiee | A61B 17/0057 |
| 2017/0128077 A1* | 5/2017 | Hewitt | A61B 17/12145 |
| 2017/0156734 A1 | 6/2017 | Griffin | |
| 2017/0224350 A1 | 8/2017 | Shimizu et al. | |
| 2017/0224355 A1 | 8/2017 | Bowman et al. | |
| 2017/0367713 A1* | 12/2017 | Greene, Jr. | A61B 17/12172 |
| 2018/0140305 A1* | 5/2018 | Connor | A61F 2/90 |
| 2019/0053810 A1 | 2/2019 | Griffin | |
| 2019/0110796 A1 | 4/2019 | Jayaraman | |
| 2019/0192168 A1 | 6/2019 | Lorenzo | |
| 2019/0357914 A1 | 11/2019 | Gorochow et al. | |
| 2020/0113576 A1 | 4/2020 | Gorochow et al. | |

FOREIGN PATENT DOCUMENTS

| | | |
|---|---|---|
| WO | WO1999/05977 A1 | 2/1999 |
| WO | WO2002/00139 A1 | 1/2002 |
| WO | WO-2009/132045 | 10/2009 |
| WO | WO2017/102804 A1 | 6/2017 |
| WO | WO2017/153603 A1 | 9/2017 |
| WO | WO2017/220400 A1 | 12/2017 |
| WO | WO-2016/137997 | 9/2019 |

OTHER PUBLICATIONS https://neuronewsinternational-wpengine.netdna-ssl.com/wp-content/uploads/sites/3/2016/07/Cerus-Endovascular-Contour-300x194.jpg, Available at least as early as Jul. 20, 2017.
https://neuronewsinternational-wpengine.netdna-ssl.com/wp-content/uploads/sites/3/2017/06/Contour-e1497957260381-300x194.png, Available at least as early as Jul. 20, 2017.
https://tse1.mm.bing.net/th?id=OIP.I7UU83VEASz4qcSv6e8cLgEsCF&pid=15.1, Available at least as early as Jul. 20, 2017.
International Preliminary Report on Patentability, PCT/US2016/019135 dated Aug. 29, 2017, 4 pages.
International Search and Written Opinion, PCT/US2016/019135 dated Jun. 6, 2016, 6 pages.
Luna, http://evtoday.com/images/articles/2017-02/0217-endovascular-fig1.png, Available at least as early as Jul. 20, 2017.
Pipeline (Medtronic), https://tse1.mm.bing.net/th?id=OIP.A6c4tqVTUI4MbkClyJDUZAEPDm&w=213&h=177&c=7&qlt=90&o=4&pid=1.7, Available at least as early as Jul. 20, 2017.
Pulsar, http://neuronewsinternational.wpengine.netdna-cdn.com/wp-content/uploads/sites/3/2016/01/first-coil-key-during-pulserider-procedures-in-wide-neck-aneurysms-300x194.jpg, Available at least as early as Jul. 20, 2017.
Surpass (stryker), http://stroke.ahajournals.org/content/40/3/952/F1.small.gif, Available at least as early as Jul. 20, 2017.
Shapiro, M., Raz, E., Becske, T., Nelson, P., "Variable Porosity of the Pipeline Embolization Device in Straight and Curved Vessels: A Guide for Optimal Deployment Strategy", Original Research

(56) References Cited

OTHER PUBLICATIONS

Interventional, Sep. 26, 2013, 6 pages, 10.3174/ajnr.A3742, American Society of Neuroradiology, Oak Brook, USA.
Perez, M., Henkes, H., Bouillot, P., Brina, O., Slater, L., Pereira, V., "Intra-aneurysmal hemodynamics: evaluation of pCONus and pCANvas bifurcation aneurysm devices using DSA optical flow imaging", Journal of NeuroInterventional Surgery, Dec. 23, 2015, 6 pages, 10.1136/neurintsurg-2015-011927, Society of NeuroInterventional Surgery, Fairfax, USA.
Invitation to Pay Additional Fees regarding International Appl. No. PCT/US2019/013909, dated Apr. 24, 2019, 14 pages.
International Search Report and Written Opinion regarding International Appl. No. PCT/US2019/013909, dated Jun. 18, 2019, 20 pps.
Torii, R., Oshima, M., Kobayashi, T., Takagi, K, and Tezduyar, T. "Fluid-structure interaction modeling of a patient-specific cerebral aneurysm: influence of structural modeling." Computational Mechanics 43: 151-159 (2008).

\* cited by examiner

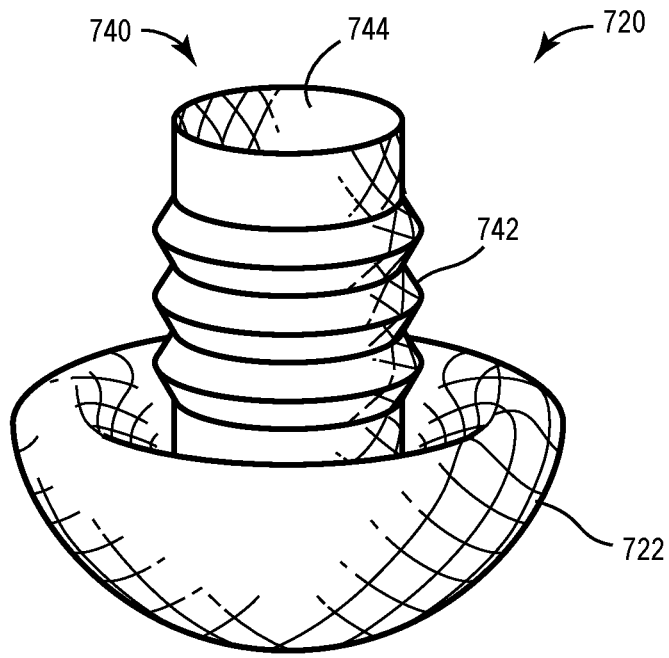
FIG. 25
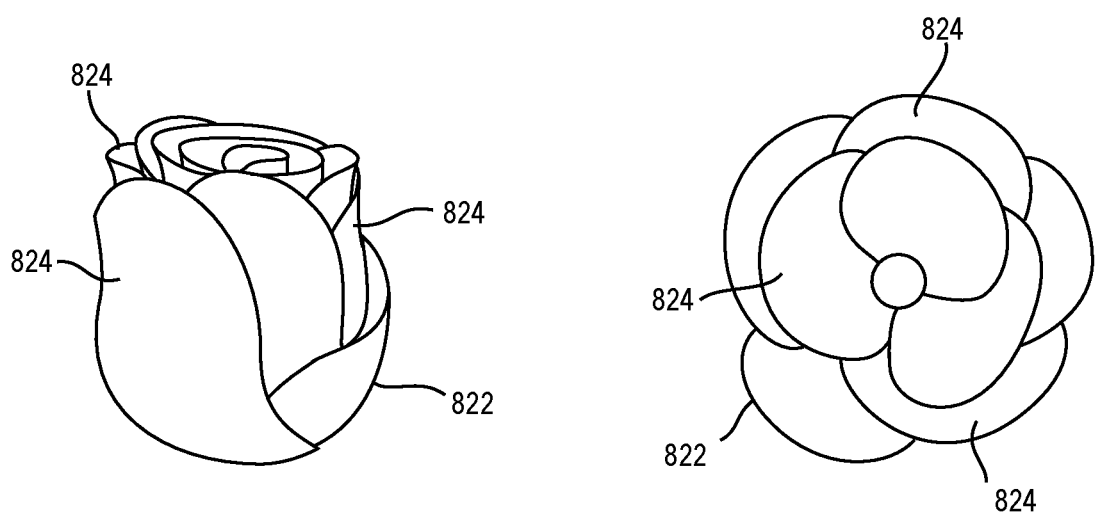
FIG. 26A
FIG. 26B

SYSTEM FOR AND METHOD OF TREATING ANEURYSMS

BACKGROUND

Aneurysms are abnormal bulging or weakening of a blood vessel, often an artery, and can have many complications. A bulging of the blood vessel can disrupt or put pressure on surrounding tissues. In the brain, this can result in a variety of side effects, such as impaired vision, impaired speech, impaired balance, etc. Further, the aneurysm creates a volume that is not along the main flow path of the blood through the blood vessel. It therefore can serve as a location for blood to become stagnant and, due to swirling eddy currents, can contribute to the formation of a thromboembolism. If the aneurysm ruptures, they can cause severe internal bleeding.

Aneurysms can be treated externally with open surgery. Such procedures typically involve closing off the entrance or "neck" of the aneurysm with a device such as vascular clamp or a ligature. However, such open surgical procedures can be highly invasive and may lead to trauma to the adjacent tissue and other side effects.

Aneurysms can also be treated through endovascular procedures. In one procedure, detachable lengths of wires (e.g., coils) are inserted into the interior volume of the aneurysm using a catheter. The coils are intended to fill the volume of the aneurysm to decrease the flow of blood into the aneurysm, inducing stagnation of flow and stimulate clotting within the aneurysm. In settings of large cerebral aneurysms, filling of the aneurysm with multiple coils can lead to mass effect that may induce brain swelling and be an independent cause for new symptoms. In another procedure, for aneurysms with a relatively large neck, the adjunctive use of stents assists with the retention of the coils within the aneurysm. This approach has a contraindication to being used when treating ruptured aneurysm, due to the need for additional anti-thrombotic medications. In another procedure, the coils are held in the volume of the aneurysm with a temporary balloon that is inflated in the blood vessel. The balloon is deflated and removed once the mass of coils is secured. In still another procedure, a stent device is placed in the artery to promote flow of blood past the aneurysm. This leads to stagnation of the blood within the aneurysm and thrombosis inside the aneurysm volume. However, a side branch of a main artery in which the stent device is placed may become trapped or "jailed", which impedes access to the side branch. In other instances, the side branch can become clotted off, possibly causing a stroke. Additionally, such a procedure generally requires the use additional anti-thrombotic medications, which limits the use of such devices in the setting of treatment of ruptured aneurysms. The stent device is generally formed with a relatively tight weave. While the tight weave increases the effectiveness of the stent device in diverting the blood flow, it also impedes or prevents access to the volume of the aneurysm or the jailed artery. In the event that the aneurysm fails to clot, the obstruction of the aneurysm by the stent device prevents the possibility of placing embolic devices inside the aneurysm. Additional procedures such as the placement of additional stents or open surgery may then be required to treat the residual.

All procedures that involve packing the volume of the aneurysm suffer from several common shortcomings. First, it can take many coils of wire to fill the volume of the aneurysm, which is time consuming and increases the time it takes to complete the procedure. Further, the coils may be compacted over time to occupy a smaller percentage of the total volume of the aneurysm. A great enough compaction of the coils can be considered a recurrence of the aneurysm and may require further treatment.

It would be advantageous to provide an improved system and method of treating an aneurysm.

SUMMARY

One embodiment relates to an apparatus for treating an aneurysm in a blood vessel includes an occlusion element disposed on a wire, the occlusion element including a cover for covering a neck of an aneurysm and an inner anchoring member. The cover is configured to expand from a compressed configuration in a tube to an expanded configuration when advanced out of a distal end of the tube to cover the neck of the aneurysm. The cover includes a sphere of mesh material formed into a hemisphere including two layers of mesh that is formed by folding a top portion of the sphere into a bottom portion of the sphere. The inner anchoring member is coupled to and extends from the second surface of the cover and is configured to contact an interior surface of the aneurysm. The inner anchoring member may be a cylindrical stem extending from a central portion of the cover.

One embodiment relates to an apparatus for treating an aneurysm in a blood vessel including an occlusion element disposed on a wire. The occlusion element includes a cover for covering a neck of an aneurysm, an inner anchoring member for contacting an interior surface of an aneurysm, and a central stem connecting the cover and the inner anchoring member. The occlusion element is coupled to the wire on an outer surface of the cover. The cover and the inner anchoring member are configured to expand from a compressed configuration while disposed in a tube to an expanded configuration when advanced out of a distal end of the tube to be positioned within the aneurysm. The cover and the inner anchoring member have a substantially similar diameter and wherein the central stem has a diameter less than the diameter of the cover and the inner anchoring member.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

These and other features, aspects and advantages of the present invention will become apparent from the following description, appended claims, and the accompanying exemplary embodiments shown in the drawings, which are briefly described below.

FIG. 25 is a schematic side view of an aneurysm occlusion device, according to an exemplary embodiment.

FIG. 26A is a schematic side view of an aneurysm occlusion device, according to an exemplary embodiment.

FIG. 26B is a schematic top view of the aneurysm occlusion device of FIG. 26A, according to an exemplary embodiment.

DETAILED DESCRIPTION

Figure 1:
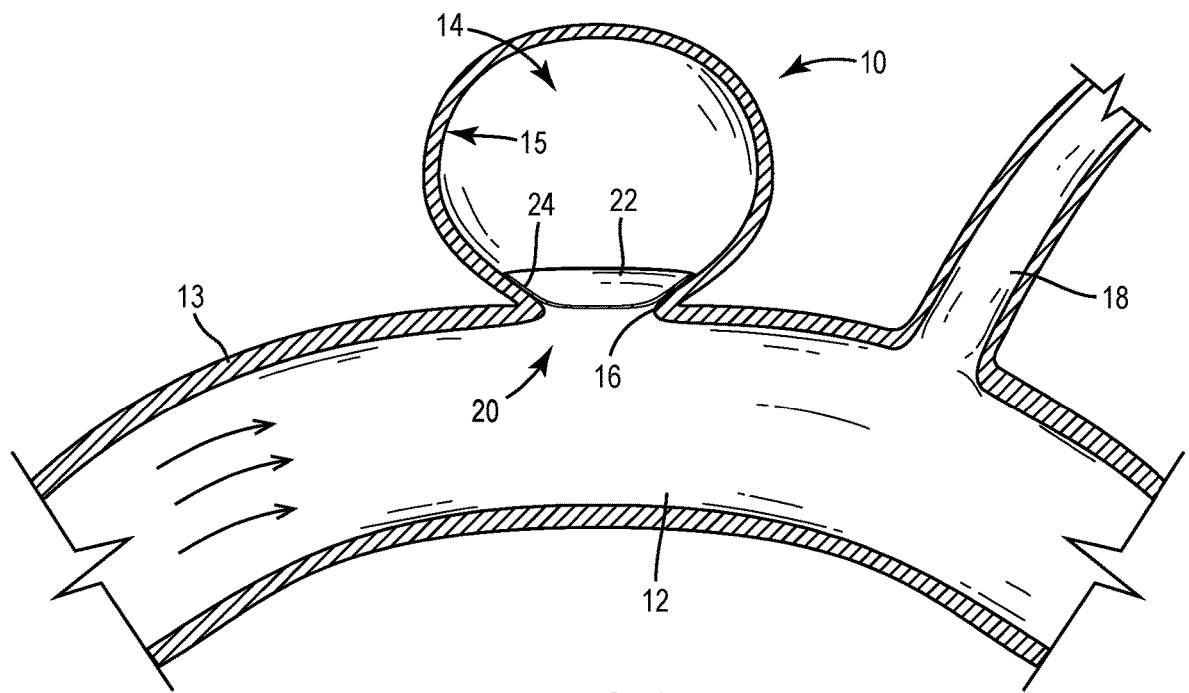
FIG. 1 is a schematic cross-section side view of an aneurysm with an endovascular device configured to occlude the aneurysm, according to an exemplary embodiment.

Referring in general to FIGS. 1-14, an aneurysm occlusion device configured to treat an aneurysm 10 is shown according to several exemplary embodiments. The aneurysm 10 is an outwardly extending bulge in the wall 13 of a blood vessel 12 and has an internal volume 14 that is in fluid communication with the blood vessel 12 through an opening at a neck portion 16. The aneurysm 10 may occur at a portion of the blood vessel 12 at which the wall 13 is weakened by disease or trauma. In one embodiment, the aneurysm 10 may be along an artery, such as a cranial artery (e.g., e.g., basilar artery, middle cerebral artery, etc.). The aneurysm 10, as depicted in the figures is exemplary only and it should be appreciated that the occlusion devices as described herein may be utilized in the treatment of aneurysms of various sizes and locations. For example, the aneurysm 10 may be located between two branches of a blood vessel.

Referring to FIGS. 1-3E, an occlusion device 20 is shown according to one exemplary embodiment disposed in the neck portion 16 of the aneurysm 10 to disrupt or halt the flow of blood flow between the vessel 12 and the internal volume 14 of the aneurysm, thereby reducing the likelihood that the aneurysm 10 will rupture. The occlusion device 20 is configured to be low profile device, minimizing disruptions to surrounding bodies, such as a side branch 18 of the blood vessel 12. The occlusion device 20 may be configured to be biodegradable or bioabsorbable material and may be configured to promote endothelialization.

The occlusion device 20 includes an inner cover 22 (e.g., plate, membrane, etc.) configured to be disposed within the internal volume 14 of the aneurysm 10. The inner cover 22 has an outer diameter that is greater than the diameter of the neck portion 16 when it is fully expanded. The inner cover 22 is a thin, flexible, concave body that can be distorted (e.g., collapsed) to be inserted through the neck portion 16 into the internal volume 14 of the aneurysm 10 (e.g., inserted by a catheter) and opened to at least partially occlude the neck portion 16. Concave, as used herein, is meant to describe any body that is contoured to have a hollow or cavity along one side. As shown in FIG. 1, in one exemplary embodiment, the inner cover 22 may be generally dome-shaped. In another embodiment, the inner cover 22 may have another concave shape (e.g., conical) that is disposed in the neck portion 16 and opens into the internal volume 14. In one embodiment, cover 22 can be disk shaped.

The inner cover 22 is formed from a flexible (e.g., soft) biocompatible material that can be collapsed into a microcatheter for endovascular delivery to the aneurysm 10. The flexibility of the inner cover 22 allows it to conform to the shape of the interior surface 15 of the aneurysm 10 and more effectively impeded the flow of blood between the aneurysm 10 and the blood vessel 12. Closely conforming to the shape of the interior surface 15 of the aneurysm 10 also facilitates the adhesion of the inner cover 22 to the tissue of the aneurysm 10 and the formation of new tissue to close off the neck portion 16.

Figure 2:
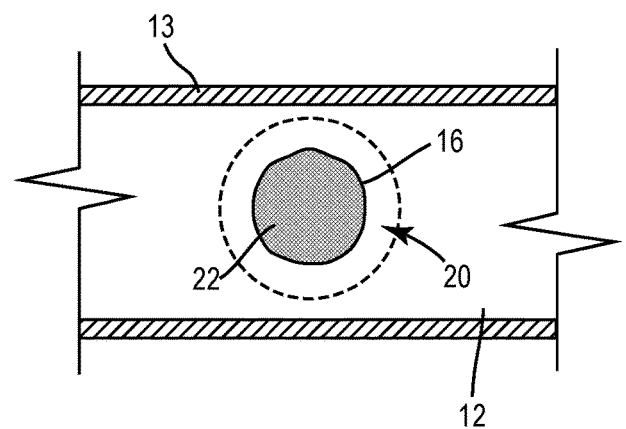
FIG. 2 is schematic cross-sectional bottom view of the aneurysm occlusion device of FIG. 1.

The inner cover 22 may be sized to fit a specific aneurysm 10. As shown in FIGS. 1-2, the inner cover 22 has a diameter that is greater than the diameter of the neck portion 16 such that a peripheral portion 24 of the inner cover 22 contacts the interior surface 15 of the aneurysm 10. The flexibility of the inner cover 22 allows the inner cover 22 to be oversized relative to the size of the neck portion 16 without damaging (e.g., rupturing) the aneurysm 10. For example, an inner cover having a diameter of approximately 5 mm may be utilized to occlude an aneurysm having a neck portion with a diameter of up to 4 mm; an inner cover having a diameter of approximately 8 mm may be utilized to occlude an aneurysm having a neck portion with a diameter of 4-6 mm; and an inner cover having a diameter of approximately 12 mm may be utilized to occlude an aneurysm having a neck portion with a diameter of 6-10 mm.

In one embodiment, the inner cover 22 may be formed from a biocompatible metal or metal alloy, such as platinum, stainless steel, titanium, a titanium-nickel alloy (e.g., nitinol). For example, the inner cover 22 may be a concave disk formed from sheet-cut nitinol. The nitinol alloy may be configured to undergo a secondary heat setting to form the desired concave shape. According to an exemplary embodiment, the inner cover 22 may have a thickness of less than 100 microns, to achieve a desired flexibility. In another embodiment, the inner cover 22 may be formed as a relatively dense mesh such as 37 micron mesh formed by a plurality of wires or fibers that are coupled together (e.g., welded, soldered, woven, etc.).

In another embodiment, the inner cover 22 may be formed from a biocompatible polymer, such as polytetrafluoroethylene (PTFE), modified polyurethane, silicone or other suitable polymer. In still other exemplary embodiments, the inner cover 22 may be formed from a metal or alloy that is coated with a polymer (e.g., parylene, PTFE, PFE, etc.) to increase lubricity and biocompatibility and to reduce thrombogenicity. The inner cover 22 may be formed as a solid sheet or membrane or may be a relatively dense mesh. In some embodiments, the inner cover 22 may include laser drilled nylon sheeting to provide a matrix for endothelialization, while reducing the bulk of the segment. Another embodiment may involve two photon polymerization, or 3-D printing of a biocompatible material to form the inner cover 22 directly onto the delivery system, or to overlie a skeleton frame which is attached to the delivery system, allowing customization of the final shape of the inner cover 22 at the time of treatment.

Figure 3A:
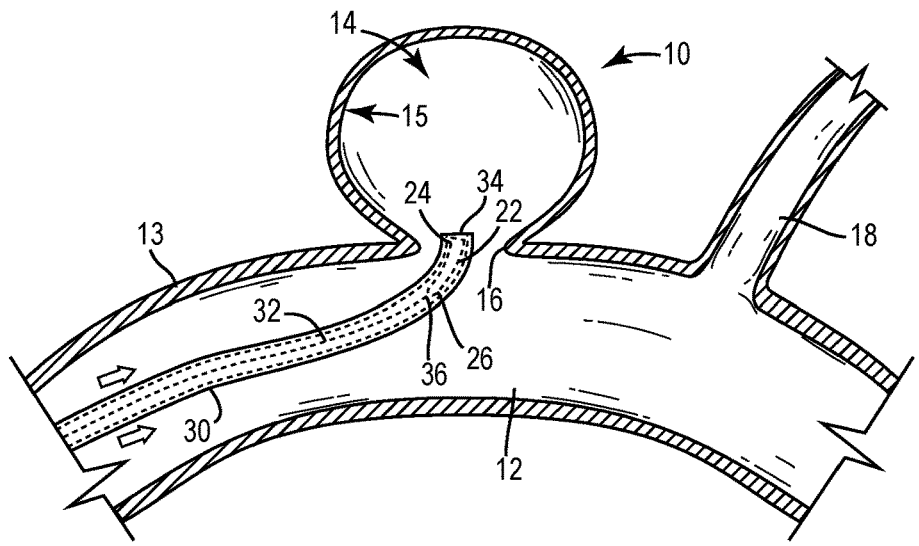
FIGS. 3A-3E are schematic side cross-section views of a catheter deploying the aneurysm occlusion device of FIG. 1, according to an exemplary embodiment.
Figure 3B:
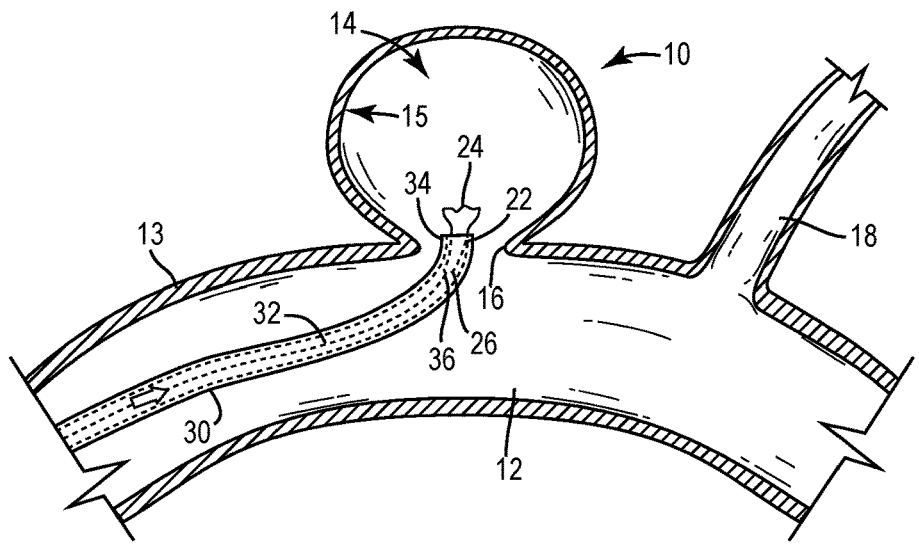

Referring now to FIGS. 3A-3D, the inner cover 22 is shown being deployed by way of a catheter 30 according to an exemplary embodiment. Referring to FIG. 3A, the catheter 30, including a push wire 32, is advanced through the blood vessel 12 to the location of the aneurysm 10. A distal end 34 of the catheter 30 is advanced through the neck portion 16 and into the internal volume 14 of the aneurysm 10 or to a portion of the blood vessel 12 proximate the neck portion 16. The push wire 32 is positioned within a lumen formed in the catheter 30. The catheter 30 may have a single lumen or the push wire 32 may be positioned within one of several lumens formed within the catheter 30. The inner cover 22 is coupled to a distal end 36 of the push wire 32 and is housed, in a collapsed configuration, within the lumen. In the collapsed configuration, the peripheral portion 24 of the inner cover 22 is upstream (e.g., closer to the distal end 34) compared to a central portion 26 to which the push wire 36 is coupled. Referring to FIG. 3B, the push wire 32 is moved within the lumen relative to the catheter 30 until the inner cover 22 begins to emerge from the end 34 of the catheter 30. The inner cover 22 is configured to expand (e.g., due to the internal spring forces of the inner cover 22) into an expanded configuration within the internal volume 14 as it clears the end 34 of the catheter 30. The push wire 32 may be moved relative to the catheter 30 by holding the catheter 30 stationary while the push wire 32 is advanced (e.g., pushing), by holding the push wire 32 stationary and retracting the catheter 30 (e.g., unsheathing), or by a combination of movements of the catheter 30 and the push wire 32. The inner cover 22 may be partially deployed with the distal end 34 of the catheter 30 positioned within the blood vessel 12 or within the aneurysm 10.

Figure 3C:
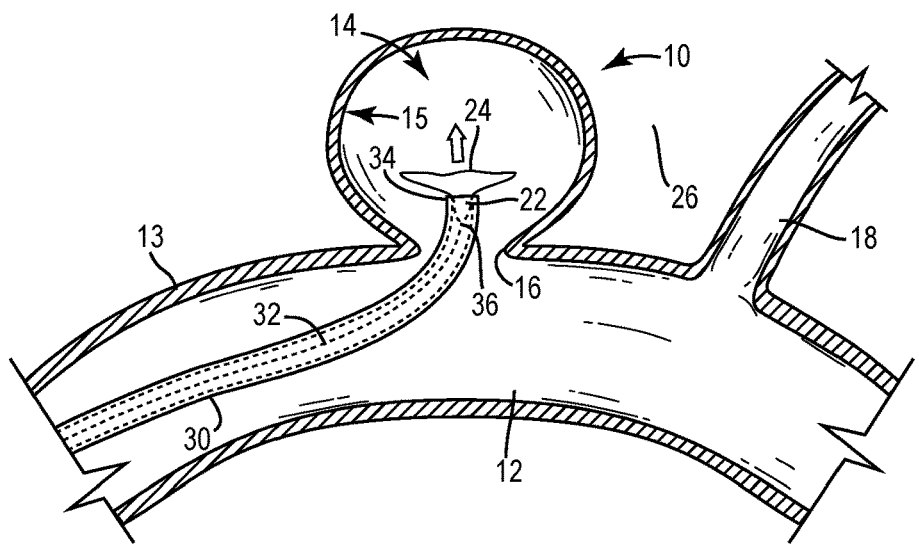
Figure 3D:
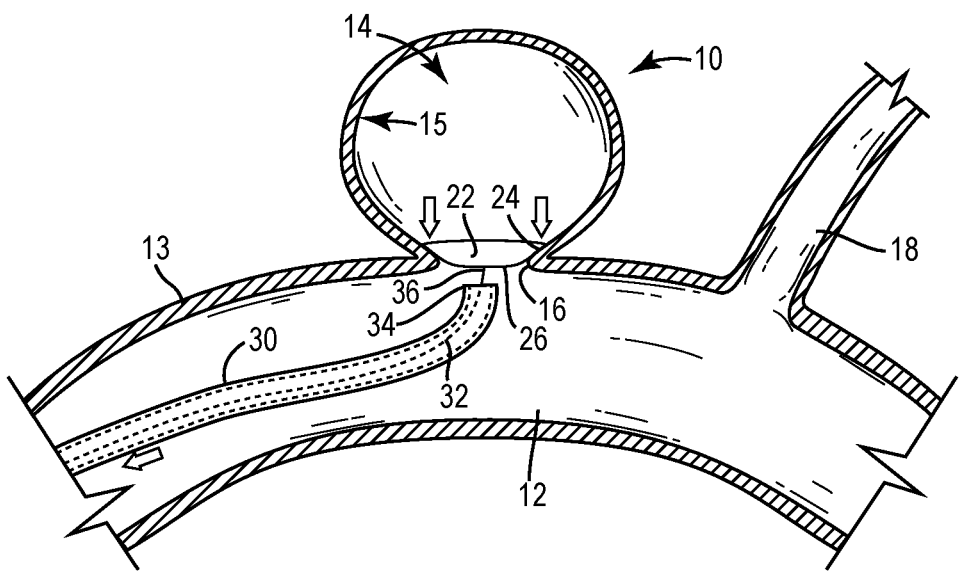
Figure 3E:
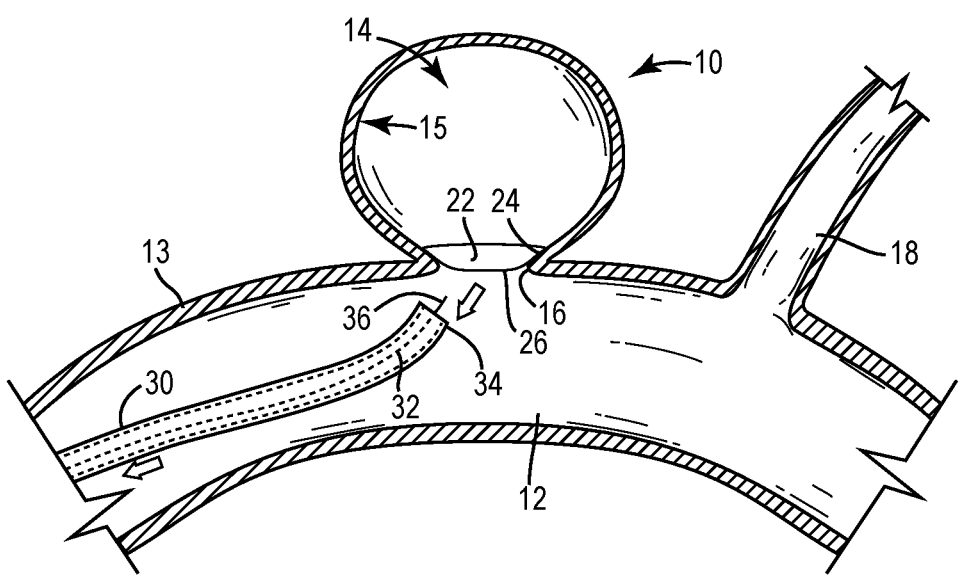

Referring to FIG. 3C, the distal end 34 of the catheter 30 is advanced into the internal volume 14 of the aneurysm 10 before the inner cover 22 is fully deployed from the catheter 30. Referring to FIG. 3D, with the inner cover 22 deployed from the catheter 30, the catheter 30 and/or the push wire 32 is retracted until the inner cover 22 is seated against the interior surface 15 of the aneurysm. Referring to FIG. 3E, the distal end 36 of the push wire 32 is detached from the inner cover 22 such that the catheter 30 and the push wire 32 may be withdrawn from the blood vessel 12 while the inner cover 22 remains in the neck portion 16 or lower portion of the aneurysm 10. The push wire 32 may be detached from the inner cover 22 by any suitable electrical or mechanical cutting device. Alternatively, the inner cover 22 can be removed by retracting the wire 32, causing cover 22 to engage distal end of tube 30 and be slid off wire 32.

In one embodiment, the inner cover 22 can be formed to be biased toward the open, expanded position. In another embodiment, the inner cover 22 can include a mesh supported by rib members or splines radiating outwardly form a center of inner cover 22. The rib members or splines may be biased toward an open position in one embodiment. In one embodiment, the rib members and splines operate in an upside down umbrella operation fashion and lock in the fully open position once the fully open position is reached.

Figure 4:
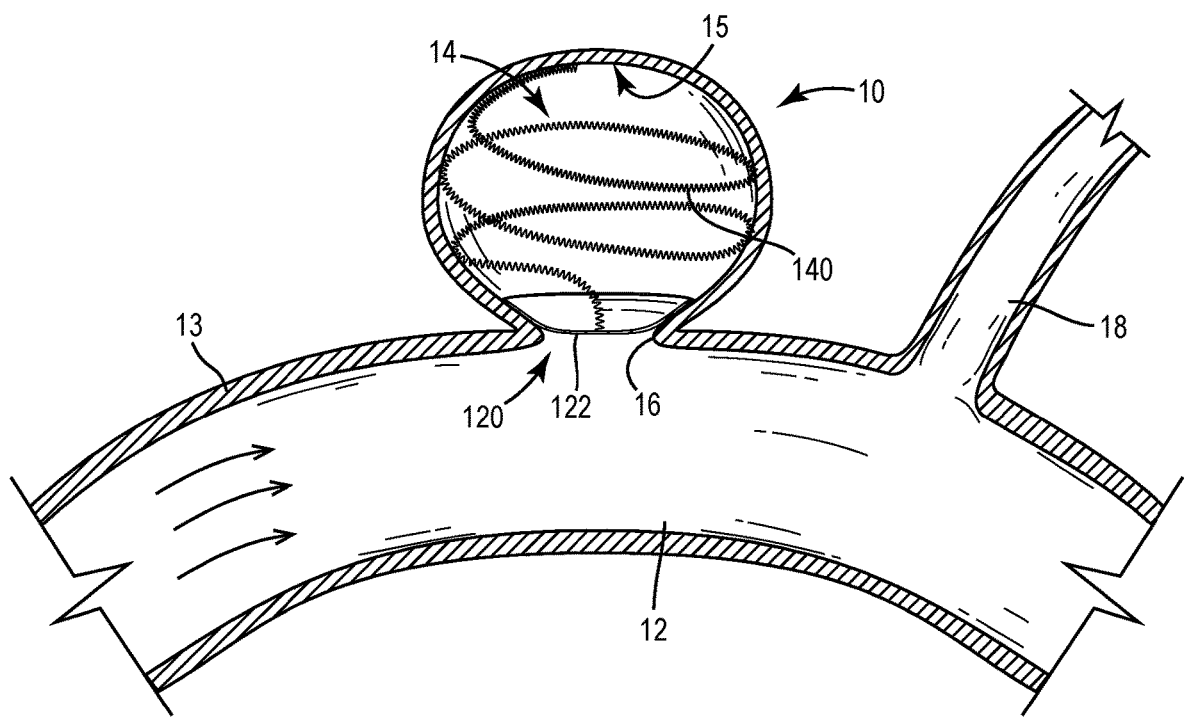
FIG. 4 is a schematic cross-section side view of an aneurysm with an endovascular device configured to occlude the aneurysm, according to another exemplary embodiment.
Figure 5:
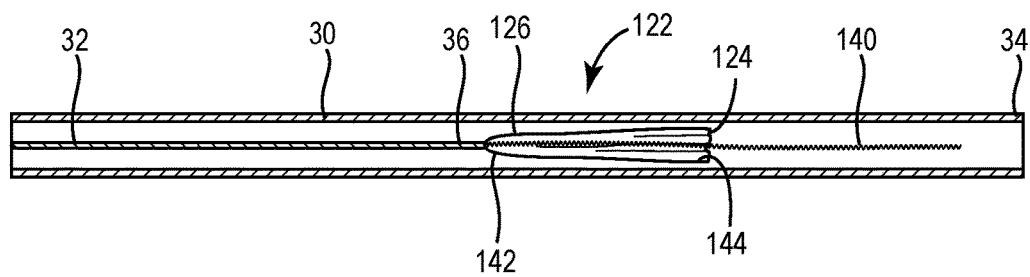
FIG. 5 is a schematic cross-section view of the occlusion device of FIG. 4 inside of a catheter, according to an exemplary embodiment.

Referring now to FIG. 4-5, an occlusion device 120 is shown according to an exemplary embodiment disposed in the lower portion of the aneurysm 10 to disrupt or halt the flow of blood flow between the vessel 12 and the internal volume 14 of the aneurysm, thereby reducing the likelihood that the aneurysm 10 will rupture. The occlusion device 120 is configured to be low profile device, minimizing disruptions to surrounding bodies, such as a side branch 18 of the blood vessel 12. The occlusion device 120 may be configured to be biodegradable or bioabsorbable material and may be configured to promote endothelialization.

The occlusion device 120 includes an inner cover 122 (e.g., plate, membrane, etc.) disposed within the internal volume 14 of the aneurysm 10 and similar to the inner cover 22 described above. The occlusion device 120 further includes an inner anchoring member 140 disposed within the aneurysm 10. The inner anchoring member 140 is configured to anchor the inner cover 122 within the aneurysm 10 near the neck portion 16. The inner anchoring member 140 provides a relatively rigid body that supports the inner cover 122 and reduces the likelihood that the inner cover 122 will be displaced from the neck portion 16 by the fluid pressure of the blood in the blood vessel 12.

According to an exemplary embodiment, the inner anchoring member 140 includes one or more loops of a coil formed from a suitable biocompatible metal or alloy (e.g., platinum, stainless steel, nickel-titanium alloy, etc.). The metal coil may be similar to the coils that are typically utilized in an endovascular coiling procedure. The inner anchoring member 140 is coupled to the inner cover 122 and includes at least one coil that contacts the interior surface 15 of the aneurysm 10. The loops of the inner anchoring member 140 do not fill the entire internal volume 14 or a substantial portion of the internal volume 14. Instead, the inner anchoring member 140 may include only a small number of loops. In one exemplary embodiment, the inner anchoring member 140 may include a single loop of the coil. In another embodiment, the anchoring member 140 includes a large number of loops substantially filing the internal volume 14. The orientation, number, and size of the loops of the inner anchoring member 140 may vary depending on the size and shape of the aneurysm 10.

Referring now to FIG. 5, the inner cover 122 and the inner anchoring member 140 are shown disposed within a catheter 30 according to an exemplary embodiment. The inner cover 122 is coupled to a distal end 36 of the push wire 32 and is housed, in a collapsed configuration, within the lumen of the catheter 30. In the collapsed configuration, the peripheral portion 124 of the inner cover 122 is upstream (e.g., closer to the distal end 34) compared to a central portion 126 to which the push wire 36 is coupled on a first surface 144. The inner anchoring member 140 is coupled to a second surface 146 of the inner cover 122 opposite the first surface 142 and is disposed within the lumen of the catheter 30 upstream of the inner cover 122.

The occlusion device 120 including the inner cover 122 and the inner anchoring member 140 is deployed within the aneurysm 10 similar to the process described above with reference to FIGS. 3A-3E. With the distal end 34 of the catheter 30 positioned proximate to the neck portion 16 of the aneurysm 10, the push wire 32 is moved within the lumen relative to the catheter 30. The push wire is moved to cause the anchoring member 140 to reach the internal volume 14 and coil within the internal volume 14.

In one embodiment, the push wire 32 has a circular solid cross section and anchoring member 140 has a coiled cross section (e.g., like a telephone cord) to facilitate coiling in the internal volume 14. In one embodiment, the push wire 32 and the anchoring member 140 have a circular solid cross section. In one embodiment, the push wire 32 and anchoring member have a coiled solid cross section.

After coiling of the anchoring member 140 is complete, the inner anchoring member 140 is pushed out of the catheter and into the internal volume 14, where it contacts the interior surface 15 of the aneurysm 10. The push wire 32 is moved further until the inner cover 122 begins to emerge from the end 34 of the catheter 30 to expand into the expanded configuration within the internal volume 14. The catheter 30 and/or the push wire 32 is then retracted until the inner cover 122 is seated against the interior surface 15 of the aneurysm 10 and held in place by the inner anchoring member 140. The distal end 36 of the push wire 32 is detached from the first surface 146 of the inner cover 122 such that the catheter 30 and the push wire 32 may be withdrawn from the blood vessel 12 while the inner cover 122 remains in the neck portion 16 or the lower portion of the aneurysm 10 with the inner anchoring member 140 coupled to the second surface 146.

Figure 6:
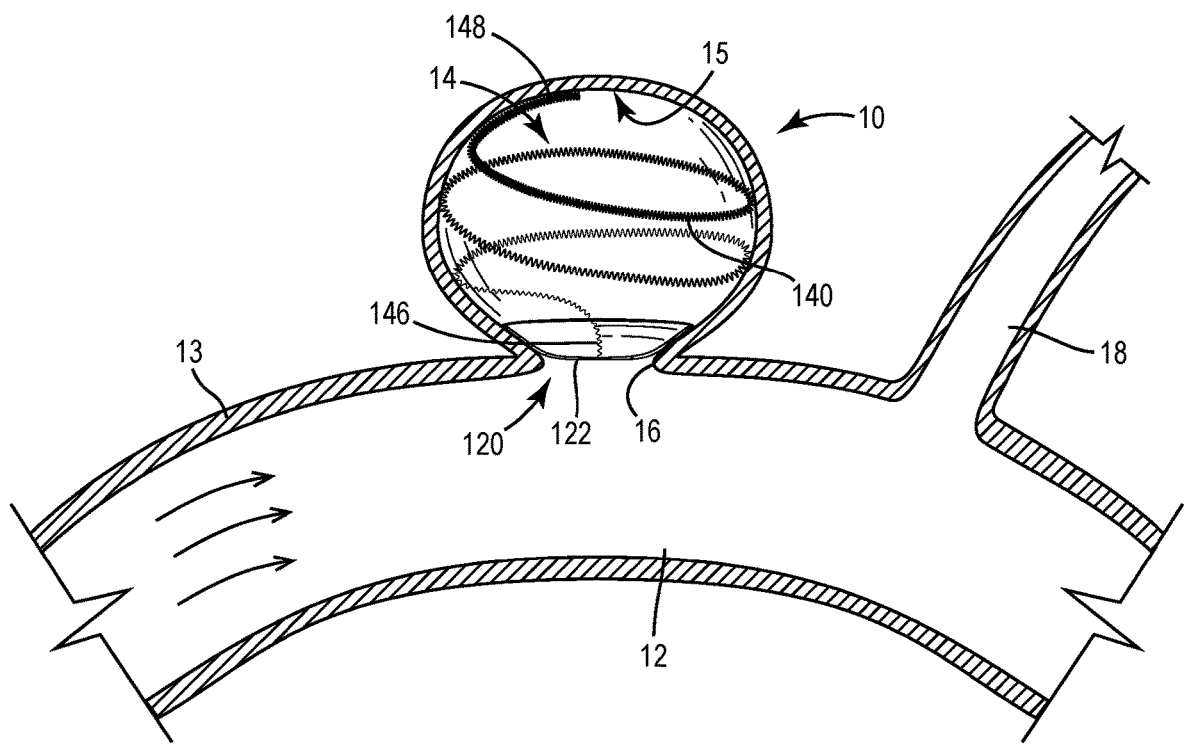
FIG. 6 is a schematic cross-section side view of an aneurysm with an endovascular device configured to occlude the aneurysm, according to another exemplary embodiment.

Referring to FIG. 6, in one exemplary embodiment, the anchoring member 140 may have a variable stiffness. For example, the inner anchoring member 140 may be relatively pliable at a proximal end 146 and relatively stiff at a distal end 148. The relatively stiff distal end 148 may be configured to provide additional support to strengthen the walls of the aneurysm 10. The stiffer portions of the inner anchoring member 140 may be utilized as framing members to create a structure in the internal volume 14 of the aneurysm while the more pliant portions are utilized to fill in the internal volume of the aneurysm and support the inner cover 122. The stiffness of the inner anchoring member 140 may be controlled in a variety of ways, such as by varying the thickness of the coil, the radius of the coil, and/or by varying the material used to form the coil.

The more pliant portions of the inner anchoring member may include a removable sheath or layer to facilitate the positioning of the stiffer portions of the inner portions of the anchoring member 140 within the aneurysm 10. The sheath may be removed once the distal end 148 and the stiffer portions of the inner anchoring member 140 are positioned.

In one embodiment, the stiffness of the inner anchoring member 140 may transition smoothly or incrementally along the length of the inner anchoring member 140 between the distal end 148 and the proximal end 146. In other exemplary embodiments, the inner anchoring member 140 may include two or more distinct zones or portions, each with a different stiffness or other characteristic. The inner anchoring member 140 may include markers or other indicators to delineate the transition from one zone to another. In one embodiment, the indicators may be external, such as indicators provided on an outer shaft coupled to the push wire, each of the outer indicators corresponding to the transition from a zone with a first stiffness to a zone with a second stiffness. In another embodiment, the indicators may be internal, such as radiopaque indicators (e.g., a platinum coating) on the inner anchoring member 140 between the zones.

In one embodiment, the anchoring member 140 with a variable stiffness can be utilized without the inner cover 122. In such an embodiment, the anchoring member 140 fills the internal volume 14. In one embodiment, a number of anchoring members 140 can be utilized. In one embodiment, the first employed anchoring member 140 has a varying stiffness (e.g., thickness) that is greater than the varying stiffness (e.g., thickness) of the next employed anchoring member.

Referring now to FIG. 7-10, an occlusion device 220 is shown according to an exemplary embodiment disposed in the lower portion of the aneurysm 20 near or at the neck portion 26 to disrupt or halt the flow of blood flow between the vessel 22 and the internal volume 14 of the aneurysm 20, thereby reducing the likelihood that the aneurysm 20 will rupture. The occlusion device 220 is configured to be low profile device, minimizing disruptions to surrounding bodies, such as a side branch 28 of the blood vessel 22. The occlusion device 220 may be configured to be biodegradable or bioabsorbable material and may be configured to promote endothelialization.

The occlusion device 220 includes an inner cover 222 (e.g., plate, membrane, etc.) disposed within the internal volume 14 of the aneurysm 10 and similar to the inner cover 22, 122 described above. Occlusion device 220 also includes an inner anchoring member 240 disposed within the aneurysm 10 and similar to the inner anchoring member 140 described above. The inner anchoring member 240 is configured to anchor the inner cover 222 within the aneurysm 20 near or at the neck portion 16. The occlusion device 220 further includes an outer anchoring member 250 disposed within the blood vessel 12 proximate the aneurysm 10. The outer anchoring member 250 provides a relatively rigid body that supports the inner cover 222 and reduces the likelihood that the inner cover 222 will be displaced from the neck portion 16 by the fluid pressure of the blood in the blood vessel 12.

Figure 7:
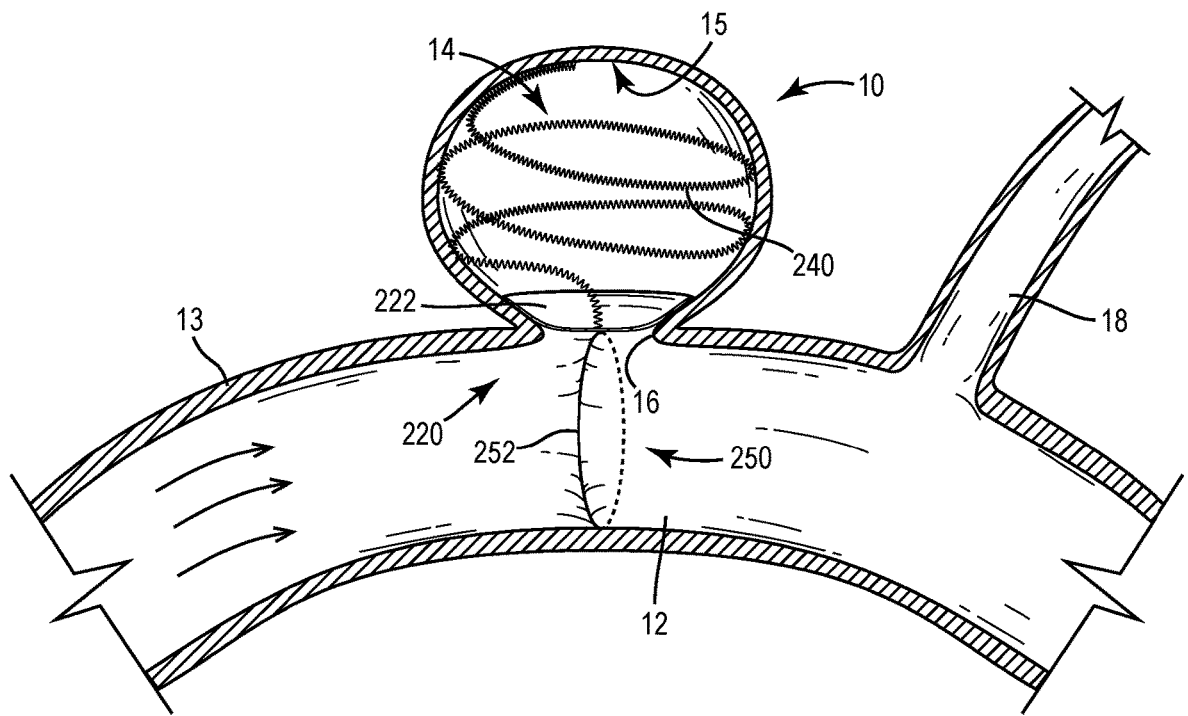
FIG. 7 is a schematic cross-section side view of an aneurysm with an endovascular device configured to occlude the aneurysm, according to another exemplary embodiment.

Referring to FIG. 7, according to an exemplary embodiment, the outer anchoring member 250 includes a loop 252 of a coil formed from a suitable biocompatible metal or alloy (e.g., platinum, stainless steel, nickel-titanium alloy, etc.). The metal coil may be similar to the coils that are typically utilized in an endovascular coiling procedure. The loops 252 is coupled to the inner cover 222 and contacts the wall 13 of the blood vessel 12 in one embodiment. The loop 252 is oriented perpendicular to the flow of blood through the blood vessel 12 in one embodiment. Multiple coils or loops 252 can be utilized in one embodiment.

Figure 8:
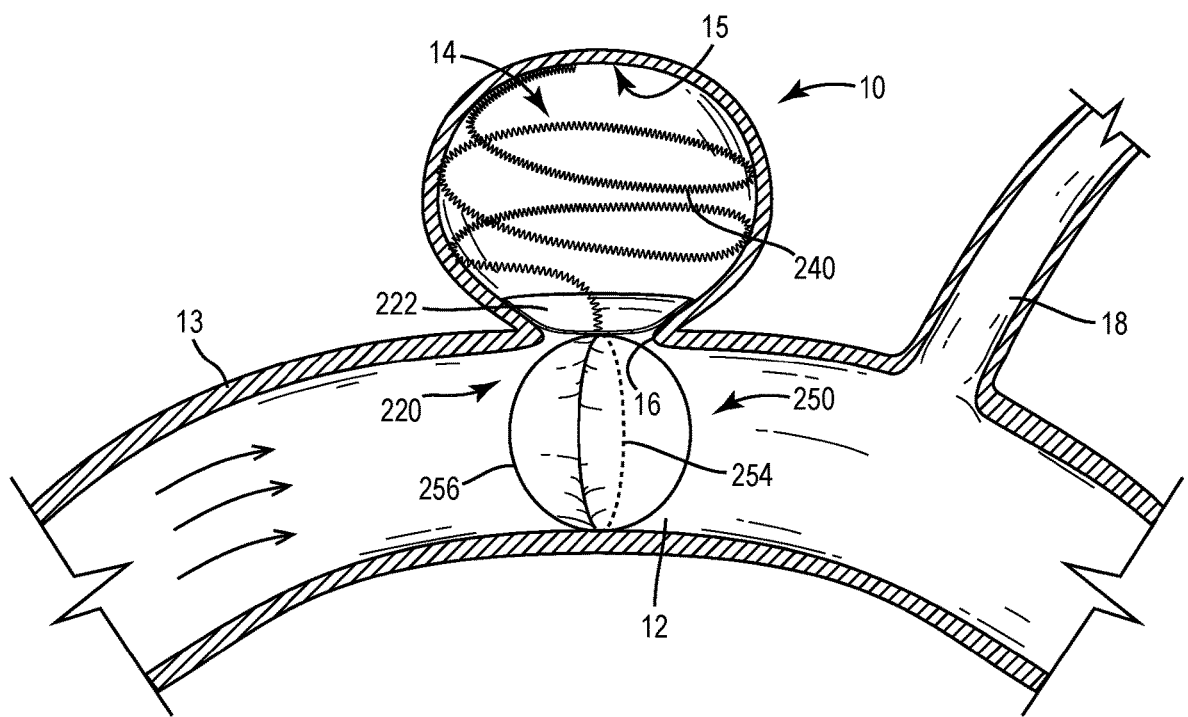
FIG. 8 is a schematic cross-section side view of an aneurysm with an endovascular device configured to occlude the aneurysm, according to another exemplary embodiment.

Referring to FIG. 8, according to an exemplary embodiment, the outer anchoring member 250 includes a first loop 254 and a second loop 256. The loops 254 and 256 may be loops of a coil formed from a suitable biocompatible metal or alloy (e.g., platinum, stainless steel, nickel-titanium alloy, etc.). At least one of the loops 254 and 256 are coupled to the inner cover 222 and contact the wall 13 of the blood vessel 12. The first loop 254 extends about the inner circumference of the blood vessel 12 such that it is oriented perpendicular to the flow of blood through the blood vessel 12. The second loop 256 is oriented parallel to the flow of blood through the blood vessel 12. The second loop 256 is formed of a coil having a fairly small diameter and does not substantially impede the flow of blood through the blood vessel. In other embodiment, the outer anchoring member 250 may include more than two loops. The orientation, number, and size of the loops may vary depending on the size and shape of the blood vessel 12.

Figure 9:
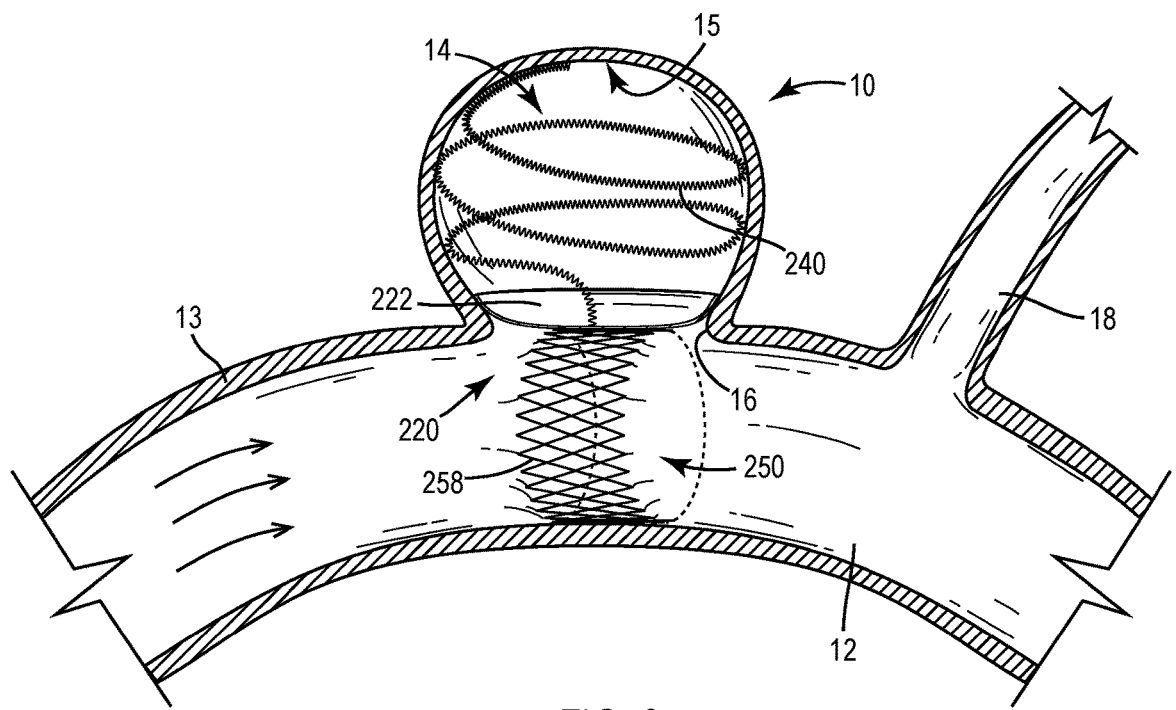
FIG. 9 is a schematic cross-section side view of an aneurysm with an endovascular device configured to occlude the aneurysm, according to another exemplary embodiment.

Referring to FIG. 9, according to another exemplary embodiment, the outer anchoring member 250 includes a stent 258 formed from a suitable biocompatible metal or alloy (e.g., platinum, stainless steel, nickel-titanium alloy, etc.) or a suitable biocompatible polymer. The stent 258 is introduced in a collapsed state to the blood vessel 12 proximate the aneurysm 10 via the catheter 30. Once deployed into the blood vessel 12, the stent 258 is expanded to engage against the walls of the blood vessel 12. The stent 258 may be self-expandable or may be expanded with another device, such as an inflatable balloon. All or part of the stent 258 may be coated or covered with a radiopaque material, such as a platinum to allow for visualization of the stent 258 (e.g., during and after the placement of the stent 258).

The stent 258 is not intended to occlude the neck portion 16 of the aneurysm 10, but instead forms a structure to facilitate the placement and anchoring of the inner cover 222. The stent 258 therefore does not need to be as wide as or wider than the neck portion 16, but may be a relatively short body (e.g., shorter than the width of the neck portion 16 of the aneurysm 10). The relatively short length of the stent 258 reduces the likelihood that the outer anchoring member 250 will disrupt surrounding bodies, such as a side branch 18 of the blood vessel 12. Further, the stent 258 may have a non-dense, relatively open configuration with variable cell morphology which may extend proximally in the blood vessel 12 from the neck portion 16. In other embodiments, the stent 258 may be a solid member, such as a band formed of a metal or alloy with a relatively thin thickness.

In another embodiment, the outer anchoring member 250 may be a temporary member that is removed with the catheter 30 after the occlusion device 320 has been placed in the neck portion 16 of the aneurysm and has been coupled to the walls of the aneurysm 10. For example, the outer anchoring member may be a balloon that is inflated in the blood vessel 12 proximate the aneurysm to provide a temporary structure to support the inner cover 222.

Figure 10:
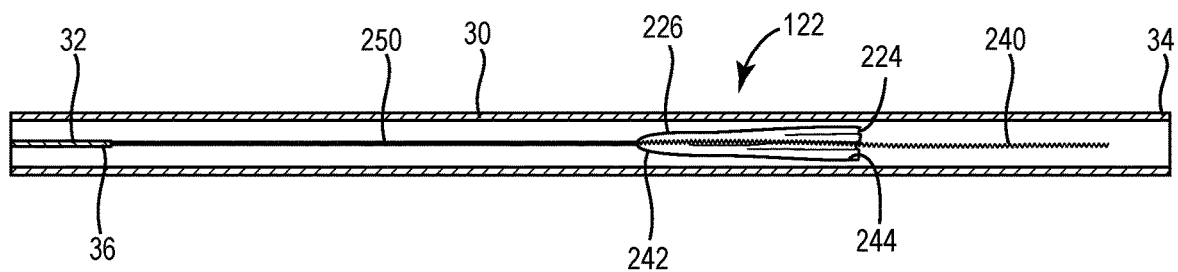
FIG. 10 is a schematic cross-section view of the occlusion device of FIG. 7 inside of a catheter, according to an exemplary embodiment.

Referring now to FIG. 10, the inner cover 222, the inner anchoring member 240, and the outer anchoring member 250 are shown disposed within a catheter 30 according to an exemplary embodiment. The outer anchoring member 250 is coupled to a distal end 36 of the push wire 32 and is housed, in a collapsed configuration, within the lumen of the catheter 30. The outer anchoring member 250 is coupled to the inner cover 222, which is housed, in a collapsed configuration, within the lumen of the catheter 30 upstream of the outer anchoring member 250. The outer anchoring member 250 may be coupled to the inner cover 222, for example, with an adhesive. In the collapsed configuration, a peripheral portion 224 of the inner cover 222 is upstream of a central portion 226 to which the outer anchoring member 250 is coupled on a first surface 244. The inner anchoring member 240 is coupled to a second surface 246 of the inner cover 222 opposite the first surface 242 and is disposed within the lumen of the catheter 30 upstream of the inner cover 222.

The occlusion device 220 including the inner cover 222 and the inner anchoring member 240 is deployed within the aneurysm 20 similar to the process described above with reference to FIGS. 3A-3E. With the distal end 34 of the catheter 30 positioned proximate to the neck portion 16 of the aneurysm 10, the push wire 32 is moved within the lumen relative to the catheter 30. The inner anchoring member 240 is pushed out of the catheter and into the internal volume 14, where is contacts the interior surface 25 of the aneurysm 20. The push wire 32 is moved further until the inner cover 222 begins to emerge from the end 34 of the catheter 30 to expand into an expanded configuration within the internal volume 14. The catheter 30 and/or the push wire 32 is then retracted until the inner cover 222 is seated against the interior surface 25 of the aneurysm 20 and held in place by the inner anchoring member 240. The push wire 32 is moved further until the outer anchoring member 250 emerges from the catheter 30. The outer anchoring member 250 may be, for example, one or more loops 252, 254, or 256, or the stent 258. The distal end 36 of the push wire 32 is detached from the outer anchoring member such that the catheter 30 and the push wire 32 may be withdrawn from the blood vessel 22 while the inner cover 22 remains near or in the neck portion 16 of the aneurysm 20 with the inner anchoring member 240 coupled to the second surface 246 and the outer anchoring member 250 disposed in the blood vessel 12. In other embodiments, the push wire 32 may be coupled directly to the inner cover 222 and the outer anchoring member 250 may be deployed separately (e.g., from another catheter).

Referring now to FIG. 11-14, an occlusion device 320 is shown according to an exemplary embodiment disposed in the neck portion 16 of the aneurysm 10 to disrupt or halt the flow of blood flow between the vessel 12 and the internal volume 14 of the aneurysm, thereby reducing the likelihood that the aneurysm 10 will rupture. The occlusion device 320 is configured to be low profile device, minimizing disruptions to surrounding bodies, such as a side branch 18 of the blood vessel 12. The occlusion device 320 may be configured to be biodegradable or bioabsorbable material and may be configured to promote endothelialization.

The occlusion device 320 includes an inner cover 322 (e.g., plate, membrane, etc.) disposed within the internal volume 14 of the aneurysm 10 and similar to the inner cover 22, 122, or 222 described above. The occlusion device 320 further includes an outer cover 360 disposed in the blood vessel 12 proximate the aneurysm 10. The outer cover 360 may be coupled to the inner cover 322 provides a relatively rigid body to support the inner cover. The outer cover 360 reduces the likelihood that the inner cover 322 will be displaced from the neck portion 16 by the fluid pressure of the blood in the blood vessel 32. The outer cover 360 may be utilized instead of or in addition to other devices, such as the inner anchoring member 140 or the outer anchoring member 250 to secure the inner cover 322 in the neck portion 16.

Figure 11:
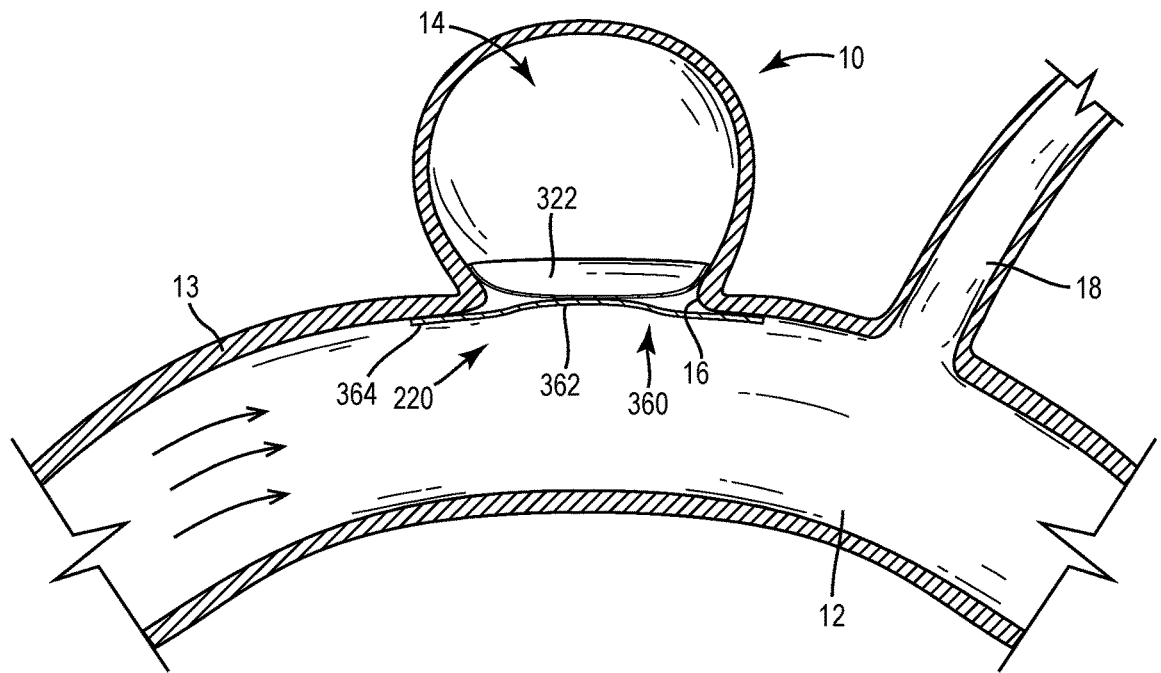
FIG. 11 is a schematic cross-section side view of an aneurysm with an endovascular device configured to occlude the aneurysm, according to another exemplary embodiment.

Referring to FIG. 11, according to an exemplary embodiment, the outer cover 360 is a relatively thin member (e.g., plate, sheet, etc.) formed from a suitable biocompatible such as a metal or alloy (e.g., platinum, stainless steel, nickel-titanium alloy, etc.), or a polymer (e.g., PTFE, etc.). According to an exemplary embodiment, the outer cover 360 has a thickness of less than 2 mm. According to a preferred embodiment, the outer cover has 360 has a thickness of less than 1 mm. The outer cover 360 is a low-profile body that does not substantially impede the flow of blood through the blood vessel 12. The outer cover 360 includes a peripheral portion 362 that contacts the wall 13 of the blood vessel 12 around the neck portion 16 of the aneurysm 10 and a central portion 364 disposed in the neck portion 16. The central portion 364 may be integrally formed with the inner cover 322 or may be coupled to the inner cover 322 (e.g., with a suitable adhesive). All or part of the outer cover 360 may be coated or covered with a radiopaque material, such as a platinum, to allow for visualization of the outer cover 360 (e.g., during and after the placement of the outer cover 360). In embodiment, outer cover 360 is attached to inner cover at a center area having less area than the neck portion 16 (e.g., 90 percent, 75 percent, or 50 percent of the area of the neck portion). In one embodiment, the center area has a circular shape.

Figure 12:
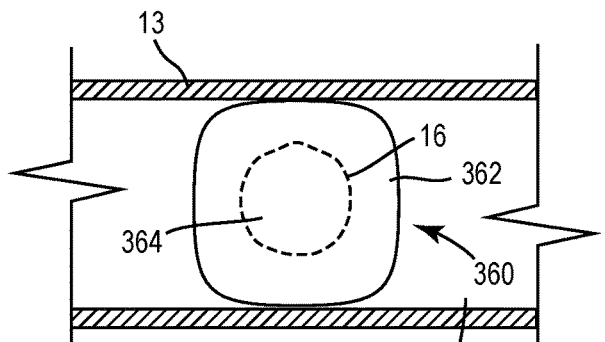
FIG. 12 is a schematic cross-sectional bottom view of an aneurysm occlusion device, according to an exemplary embodiment.

The outer cover 360 is not intended to occlude the neck portion 16 of the aneurysm 10, but instead forms a structure to facilitate anchor the inner cover 322. The outer cover 360 therefore does not need to completely cover the neck portion 16. The outer cover 360 may therefore be shaped such that portions of the neck portion 16 are uncovered and/or may be formed of a porous material (e.g., a mesh). Referring to FIG. 12, in one embodiment, the outer cover 360 may be a sheet that completely covers the neck portion 16 such that the peripheral portion 362 of the outer cover 360 extends about the entirety of the neck portion 16.

Figure 13:
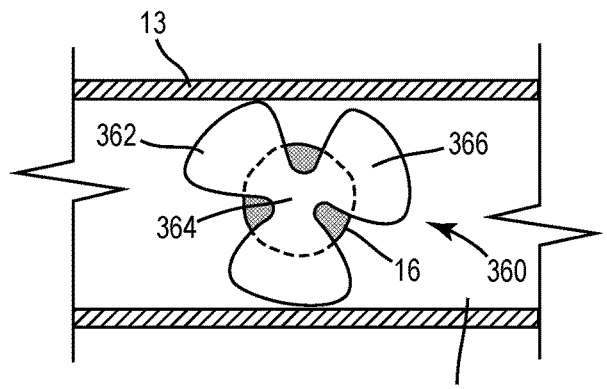
FIG. 13 is a schematic cross-sectional bottom view of an aneurysm occlusion device, according to an exemplary embodiment.

Referring to FIG. 13, in another embodiment, the outer cover 360 may include multiple segments or sections such as radial lobes 366 that extend outward from the neck portion 16. Each of the lobes 366 may include a central portion 364 disposed within the neck portion 16 and a peripheral portion 362 extending beyond the neck portion 16 to contact the wall 13 of the blood vessel 12.

Figure 14:
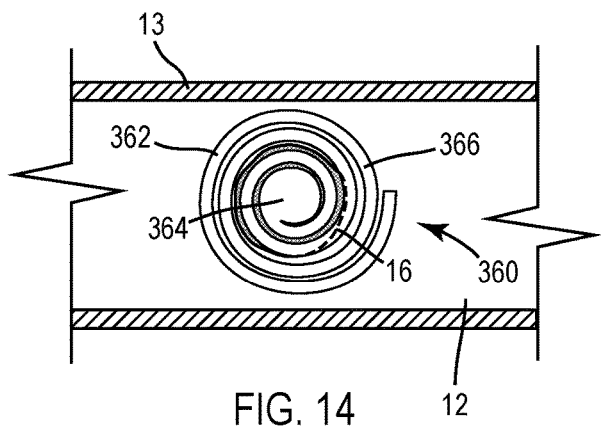
FIG. 14 is a schematic cross-sectional bottom view of an aneurysm occlusion device, according to an exemplary embodiment.

Referring to FIG. 14, in another embodiment, the outer cover 360 may include a spiral body 368. The inner loops of the spiral body 368 may form the central portion 364 while the outer loops of the spiral body 368 may form the peripheral portion 362.

The outer cover 360 may be deployed from a catheter in the same procedure as the inner cover 322. The outer cover 360 may therefore be configured to be collapsible such that it can be coupled to the inner cover 322 and housed within the catheter. The outer cover 360 may be configured such that, within the catheter, the central portion 364 is coupled to the inner cover 322 and positioned upstream of the peripheral portion 362. The inner cover 322 may be deployed as described with reference to FIGS. 3A-D. Once the inner cover 322 is deployed from the catheter and positioned in the neck portion 16, the push wire of the catheter may be advanced further to deploy the outer cover 360. The fluid pressure of the blood within the blood vessel 12 forces the outer cover 360 against the wall 13 of the blood vessel 12. In other embodiments, the push wire 32 may be coupled directly to the inner cover 322 and the outer cover 360 may be deployed separately (e.g., from another catheter).

Figure 15:
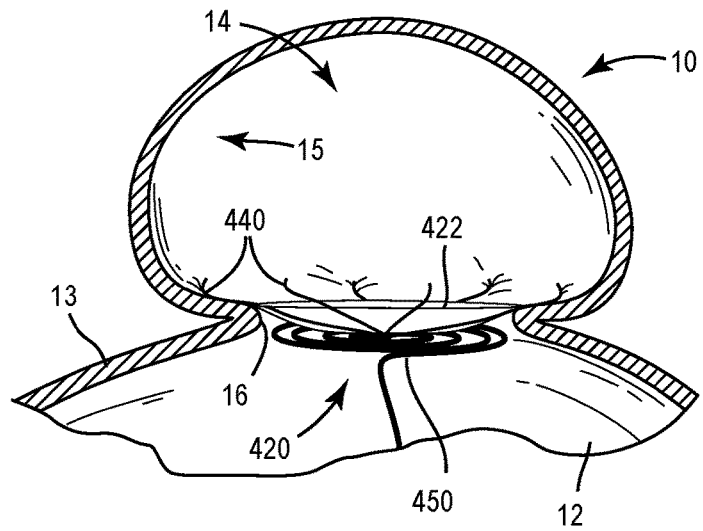
FIG. 15 is a schematic cross-sectional side view of an aneurysm with an endovascular device configured to occlude the aneurysm, according to another exemplary embodiment.
Figure 16:
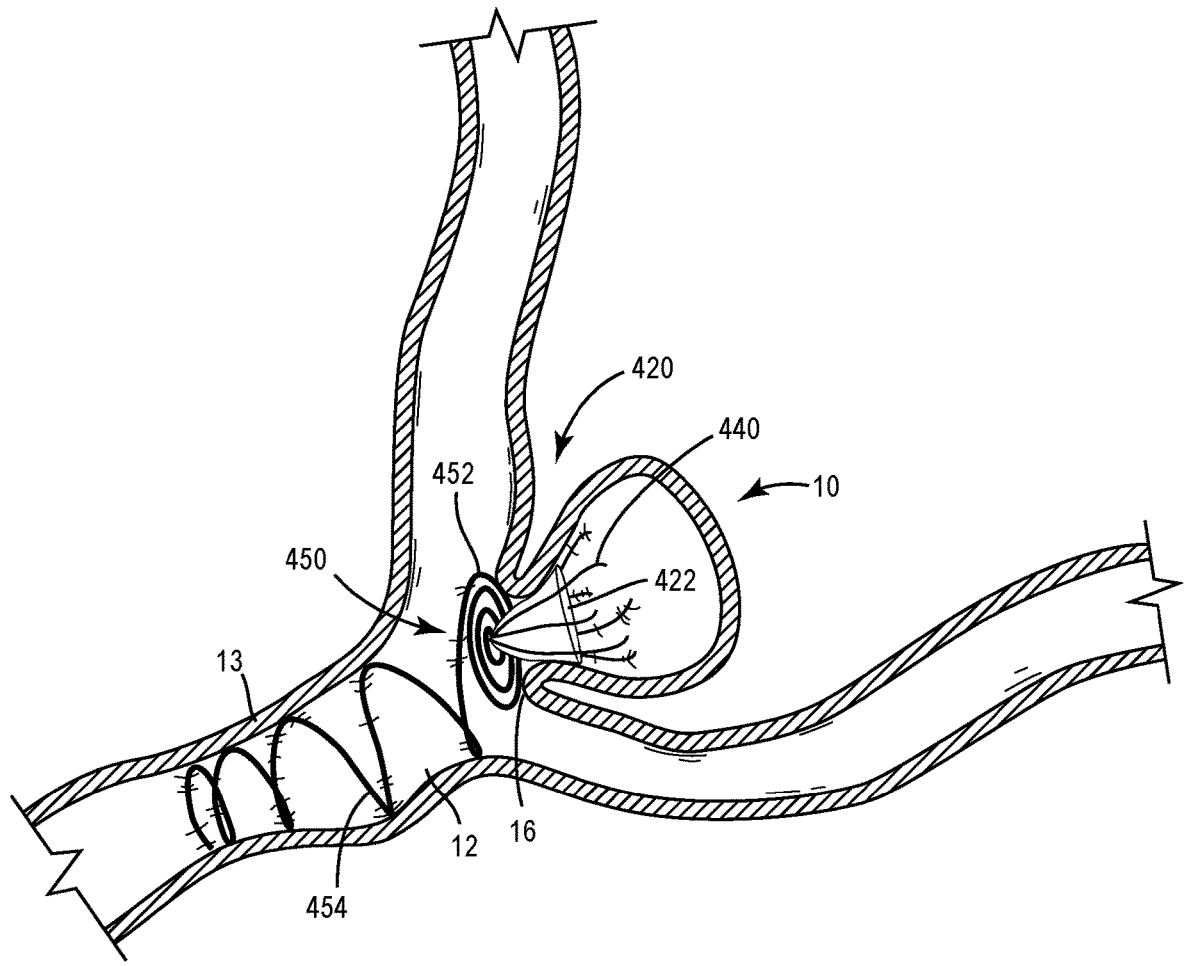
FIG. 16 is a schematic cross-sectional side view of an aneurysm with an endovascular device configured to occlude the aneurysm, according to another exemplary embodiment.

Referring now to FIGS. 15-16, an occlusion device 420 is shown according to an exemplary embodiment disposed in a lower portion, such as the neck portion 16, of the aneurysm 10. The occlusion device 420 includes an inner cover 422 (e.g., plate, membrane, etc.) disposed within the internal volume 14 of the aneurysm 10. The occlusion device 420 further includes an inner anchoring member 440 disposed within the aneurysm 10 and/or an outer anchoring member 450. The inner anchoring member 440 is configured to anchor the inner cover 422 within the aneurysm 10 in the neck portion 16. According to an exemplary embodiment, the inner anchoring member 440 includes one or more struts or arms formed from a suitable biocompatible metal or alloy (e.g., platinum, stainless steel, nick-titanium alloy, etc.). The inner anchoring member 440 is coupled to the inner cover 422 and is configured to extend beyond the periphery of the inner cover 422 to contact the interior surface 15 of the aneurysm 10. The inner anchoring member 440 may therefore be used to facilitate the positioning of the inner cover 422 in an aneurysm 10 having a relatively wide neck 16. The struts or arms of the inner anchoring member 440 do not fill the entire internal volume 14 or a substantial portion of the internal volume 14. The "mass effect" of the aneurysm 10 is reduced, as the size of the aneurysm 10 is allowed to shrink as the vessel heals, thereby reducing the pressure placed on the surrounding tissue by the aneurysm 10. The orientation, number, and length of the arms of the inner anchoring member 440 may vary depending on the size and shape of the aneurysm 10. The arms of the inner anchoring member 440 may be configured to collapse together to be delivered via a microcatheter, similar to the microcatheter 30 described above.

Referring still to FIGS. 15-16, the outer anchoring member 450 includes first portion 452 (e.g., distal portion) disposed at the neck 16 and coupled to the inner cover 422 and a second portion 454 (e.g., proximal portion) disposed in the vessel 12. The outer anchoring member 450 is formed from a suitable biocompatible metal or alloy (e.g., platinum, stainless steel, nickel-titanium alloy, etc.) or a suitable biocompatible polymer. All or part of the outer anchoring member 450 may be coated or covered with a radiopaque material, such as a platinum to allow for visualization of the outer anchoring member 450 (e.g., during and after the placement of the outer anchoring member 450). The outer anchoring member 450 is introduced in a collapsed (e.g., straightened) state to the blood vessel 12 proximate the aneurysm 10 via a catheter. Once deployed into the blood vessel 12, the outer anchoring member 450 expands such that at least a portion of the outer anchoring member compresses against the walls of the blood vessel 12. The outer anchoring member 450 may be formed as a single, continuous spiral, with loops of the spiral being formed to have variable properties (e.g., diameter, thickness, flexibility, etc.). For example, the first portion 452 may be formed to have relatively small diameter, flexible coils while the second portion 454 may be formed to have larger, relatively rigid coils providing an increased outward radial force to facilitate positioning the outer anchoring member 450 along the wall 13 of the blood vessel 12.

Figure 17:
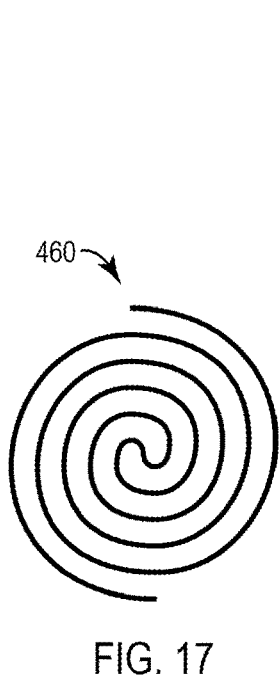
FIG. 17 is a schematic bottom view of an outer anchoring member for an aneurysm occlusion device, according to an exemplary embodiment.

Referring to FIG. 17, according to another exemplary embodiment, a portion of an outer anchoring member 460 may be formed as a dual spiral. According to other exemplary embodiments, the outer anchoring member may be formed as a wide variety of other shapes (e.g., web-shaped, star-shaped, etc.) to provide a desired flexibility and support for the inner cover at the neck of the aneurysm.

Figure 18A:
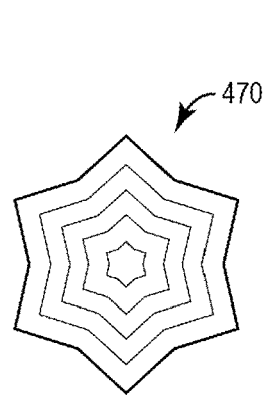
FIG. 18A is a schematic top view of a cover for an aneurysm occlusion device, according to an exemplary embodiment.
Figure 18B:
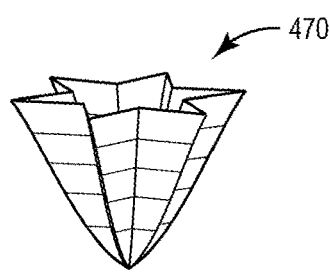
FIG. 18B is a schematic side view of the cover of FIG. 18A in a partially folded configuration.

Referring to FIGS. 18A-18B, according to another exemplary embodiment, an inner cover 470 for an occlusion device may be a star-shaped body. The inner cover 470 may be formed (e.g., creased, scored, molded) to fold and collapse along predefined fold lines.

Figure 19:
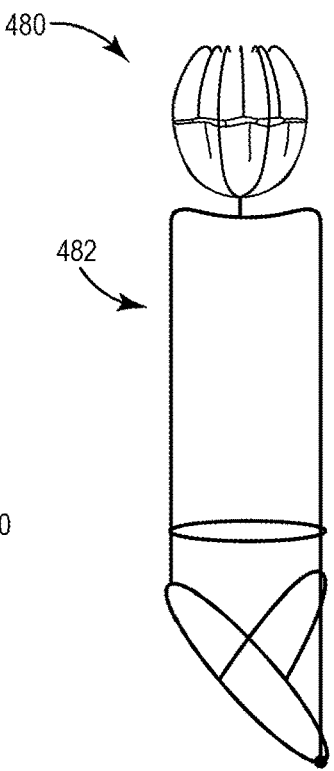
FIG. 19 is a schematic side view of an endovascular device configured to occlude an aneurysm, according to another exemplary embodiment.

Referring now to FIG. 19, an occlusion device 480 is shown having an outer anchoring member 482. The outer anchoring member 482 is a recapturable body that may be variously shaped (e.g., straight, spiral, multi-spiraled, coven, etc.). The outer anchoring member 482 is formed as a relatively open structure having a minimal number of segments that form a framework that is capable of positioning and securing the occlusion device 480 while minimizing contact with the walls of the blood vessel. The open nature of the outer anchoring member 482 has a low risk of jailing a branch blood vessel or otherwise altering the flow of blood through the blood vessel.

Figure 20:
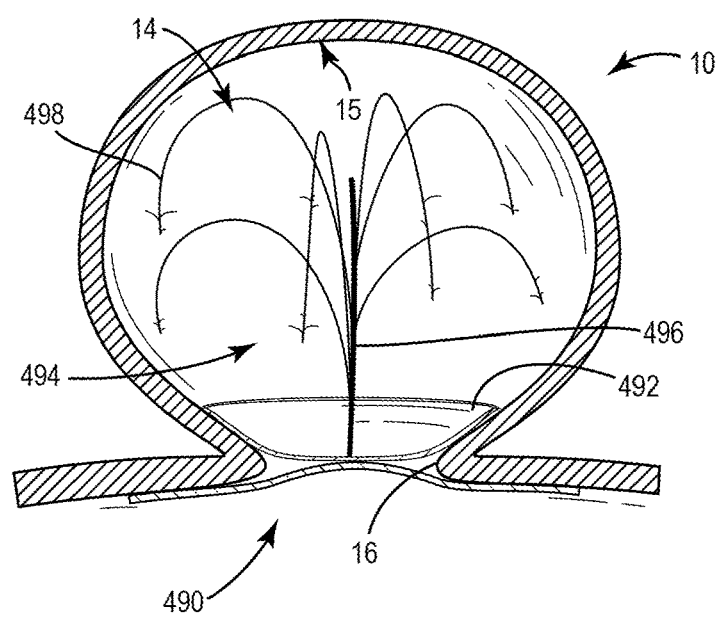
FIG. 20 is a schematic cross-sectional side view of an aneurysm with an endovascular device configured to occlude the aneurysm, according to another exemplary embodiment.

Referring to FIG. 20, an inner anchoring member 494 for an occlusion device 490 is shown according to another exemplary embodiment. The inner anchoring member 494 includes a central wire 496 coupled to the cover 492 and one or more outer wires 498 coupled to the central wire 496. The outer wires 498 extend outward from the central wire 496 to contact the interior surface 15 of the aneurysm 10. The inner anchoring member 494 is introduced in a collapsed (e.g., straightened) state to the aneurysm 10 via the catheter 30. Once deployed into the aneurysm 10, the catheter 30 is withdrawn, allowing the outer wires 498 to expand outward such that at least a portion of the outer wires 298 contact the inner surface 15 to position and anchor the cover 492 in the neck 16.

Figure 21:
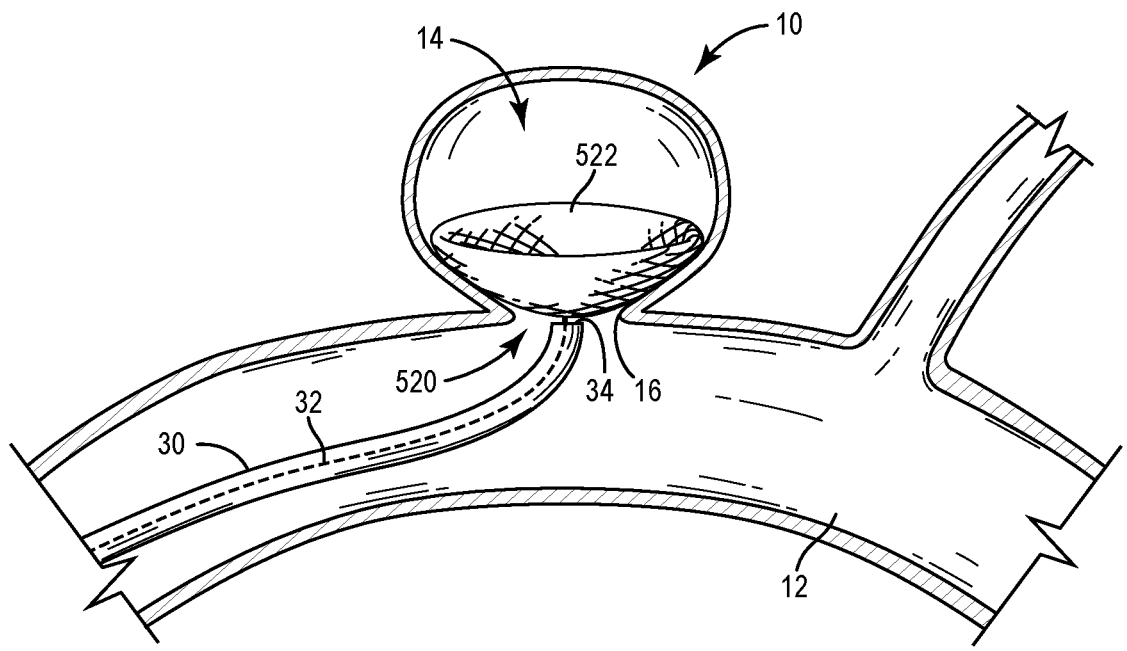
FIG. 21 is a schematic side view of an aneurysm with an endovascular device configured to occlude the aneurysm, according to another exemplary embodiment.

Referring to FIG. 21, an occlusion device 520 is shown according to an exemplary embodiment. The occlusion device 520 is disposed in or near the neck portion 16 of the aneurysm 10 to disrupt or halt the flow of blood flow between the vessel 12 and the internal volume 14 of the aneurysm 10, thereby reducing the likelihood that the aneurysm 10 will rupture. The occlusion device 520 is configured to be low profile device, minimizing disruptions to surrounding bodies, such as a side branch of the blood vessel. The occlusion device 520 may be configured to be biodegradable or bioabsorbable material and may be configured to promote endothelialization.

Figure 33:
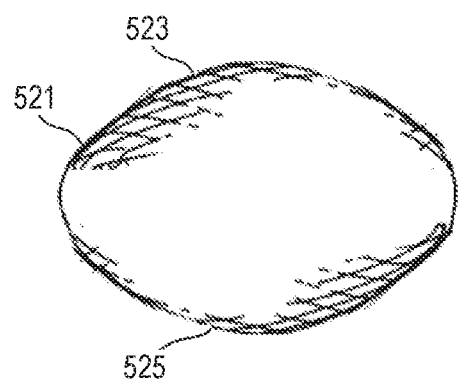
FIG. 33 is a side view of a mesh sphere, according to an exemplary embodiment.

The occlusion device 520 includes an inner cover 522 disposed within the internal volume 14 of the aneurysm 10. The inner cover 522 is disposed to cover the neck portion 16 of the aneurysm 10. The inner cover 522 is formed of a relatively dense mesh such as micron mesh formed by a plurality of wires or fibers that are coupled together (e.g., welded, soldered, woven, etc.). In this embodiment, the inner cover 522 is a double layer of mesh. The double layer of mesh is first formed as a mesh sphere. In some embodiments, the mesh sphere is collapsed into the microcatheter 30 for endovascular delivery to the aneurysm 10. As the cover 522 is released from the microcatheter 30, a push wire 32 holds an upper center portion of the mesh sphere such that the mesh sphere is released and expands into a hemispherical shape. Turning to FIG. 33, the double layered cover 522 is formed by a mesh sphere 521 wherein a first, upper portion 523 of the sphere 521 is enfolded over onto and into the second, lower portion 525 of the sphere 521, thereby forming a double-layered hemisphere shape. The expanded shape of the sphere is dependent on a distance between the upper center of the sphere and a lower center of the sphere, and can therefore be adjusted by moving the wire.

The occlusion device 520 including the inner cover 522 may be deployed within the aneurysm 20 similar to the process described above with reference to FIGS. 3A-3E. With the distal end 34 of the catheter 30 positioned proximate to the neck portion 16 of the aneurysm 10, the push wire 32 is moved within the lumen relative to the catheter 30. The inner cover 522 begins to emerge from the end 34 of the catheter 30 to expand into an expanded configuration within the internal volume 14. In one embodiment, the inner cover 522 emerges in the form of the mesh sphere. The catheter 30 and/or the push wire 32 is then retracted until the inner cover 522 is seated against the interior surface 25 of the aneurysm 10. The double layer of inner cover 522 is formed by enfolding the top portion of the sphere over the bottom portion, such as by withdrawing the push wire 32 until the top portion meets the bottom portion. In other embodiments, the inner cover 522 is deployed from the catheter 30 already in a double layered configuration and does not emerge initially as a sphere.

Figure 22:
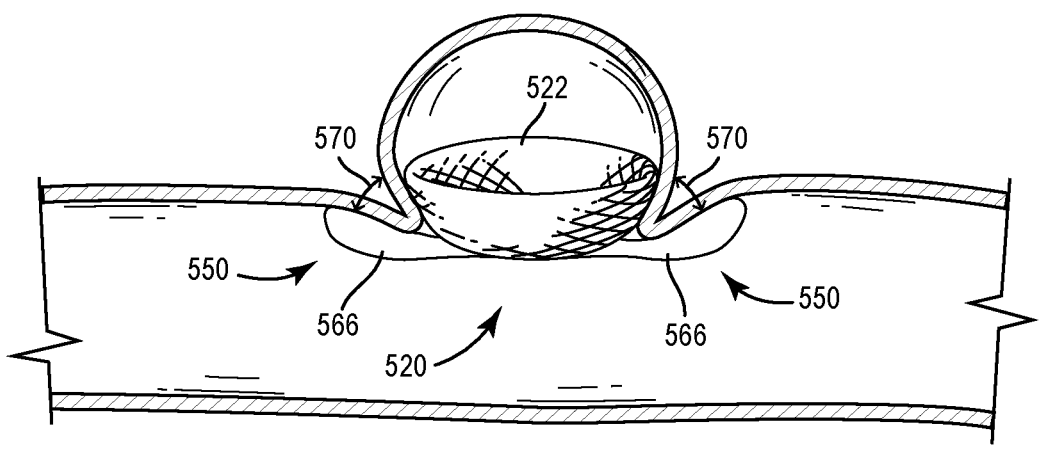
FIG. 22 is a schematic side view of an aneurysm with an endovascular device configured to occlude the aneurysm, according to another exemplary embodiment.
Figure 23A:
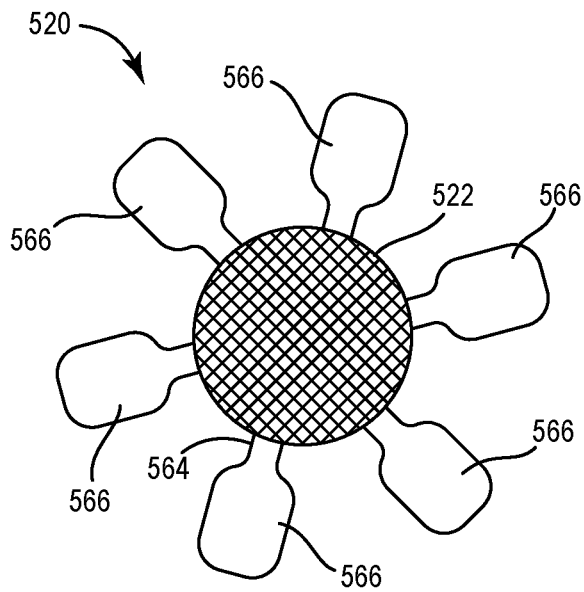
FIG. 23A is a schematic bottom view of an aneurysm occlusion device, according to an exemplary embodiment.
Figure 23B:
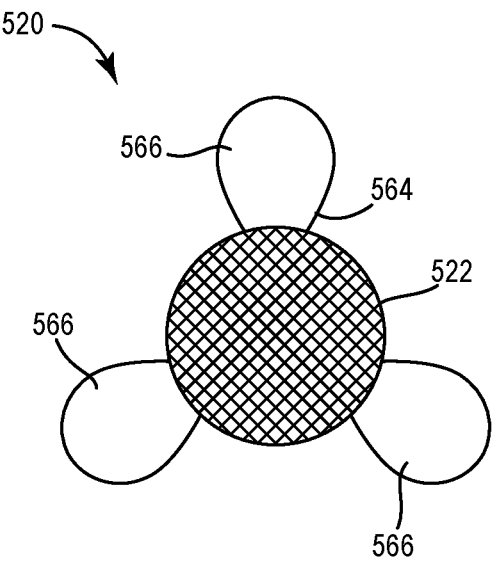
FIG. 23B is a schematic bottom view of an aneurysm occlusion device, according to an exemplary embodiment.

Referring now to FIG. 22, occlusion device 520 is shown according to another exemplary embodiment where occlusion device 520 further includes an outer anchoring mechanism 550. The outer anchoring member 550 provides support to the inner cover 522 and reduces the likelihood that the inner cover 522 will be displaced from the neck portion 16 by the fluid pressure of the blood in the blood vessel 12. In the embodiment shown, the outer anchoring mechanism 550 is formed by two or more segments or sections such as radial lobes 566 that extend outward from the neck portion 16. Each of the lobes 566 may be formed of a single wire loop made of nitinol, polymer, or similar material. Alternative to a loop, lobes 566 may be a solid, substantially flat piece of material extending from the inner cover 522. Each of the lobes 566 may include a central portion 564 configured to be disposed within the neck portion 16 and a peripheral portion 562 configured to extend beyond the neck portion 16 to contact the wall 13 of the blood vessel 12. The wire loop may be formed having a narrower portion near the central portion 564 and a wider portion near the peripheral portion 562, similar to an oar shape. In some embodiments the narrow portion and the wider portion each have a uniform diameter, as depicted in the bottom view of the occlusion device 520 shown in FIG. 23A. In other embodiments, the diameter of the loop continuously widens between a central-most portion and a peripheral-most portion, as depicted in the bottom view of the occlusion device 520 shown in FIG. 23B. Lobes 566 may take on other shapes and sizes in addition to those shown. The occlusion device 520 may have anywhere from two to eight lobes 566.

Referring back to FIG. 22, the lobes 566 of occlusion device 520 are coupled to inner cover 522 at an angle 570. In some embodiments, the angle 570 formed between the side of the inner cover 522 and the plane of the radial lobe is between 15 degrees and 45 degrees. In this way, the lobes 566 act as a clip to engage the wall 13 of the blood vessel 12 near the neck portion 16, and maintain the positioning of the occlusion device 520 in the lower portion of the aneurysm 12 near the neck portion 16.

Figure 24:
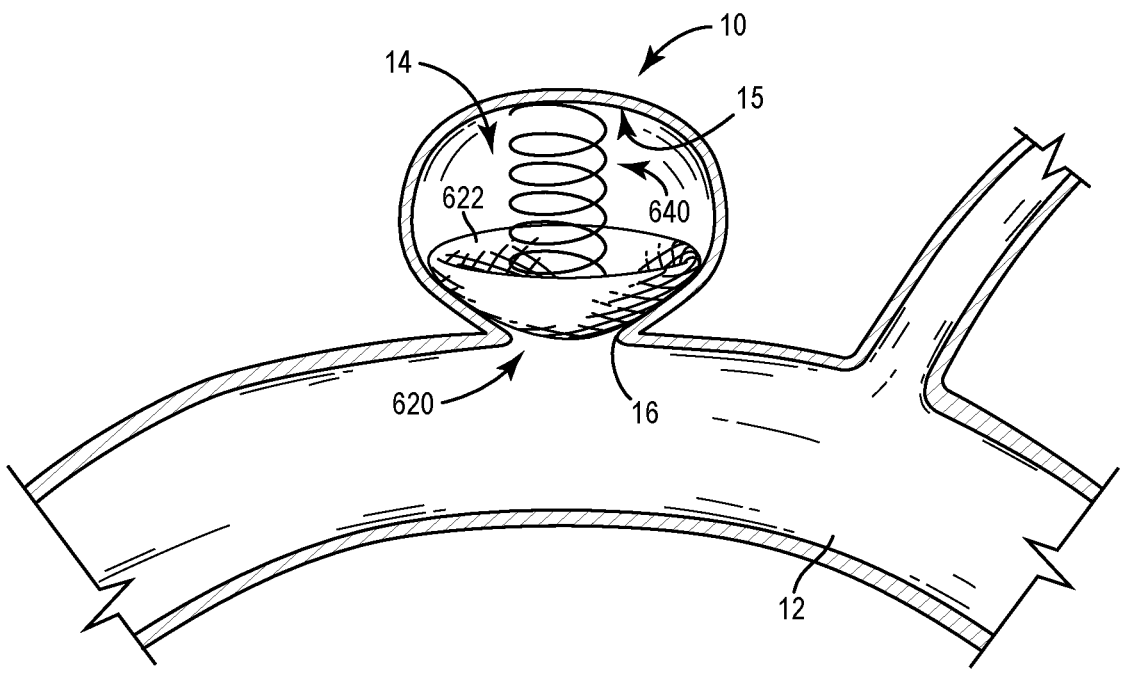
FIG. 24 is a schematic side view of an aneurysm with an endovascular device configured to occlude the aneurysm, according to another exemplary embodiment.

Referring to FIG. 24, in one exemplary embodiment, an occlusion device 620 having an inner anchoring member 640 is shown disposed within the aneurysm 10. The inner anchoring member 640 is configured to anchor the inner cover 622 within the lower portion of aneurysm 10, at or near the neck portion 16. The inner anchoring member 640 provides a relatively rigid body that supports the inner cover 622 and reduces the likelihood that the inner cover 622 will be displaced from the neck portion 16 by the fluid pressure of the blood in the blood vessel 12. According to an exemplary embodiments, the inner cover 622 is a double-layer, formed similarly to the inner cover 522. The inner cover 622 has a peripheral portion to contact the interior surface 15 of the aneurysm 10.

According to an exemplary embodiment, the inner anchoring member 640 includes one or more loops of a coil formed from a suitable biocompatible metal or alloy (e.g., platinum, stainless steel, nickel-titanium alloy, etc.). The metal coil may be spring-like and may be similar to the coils that are typically utilized in an endovascular coiling procedure. The inner anchoring member 640 is coupled to the inner cover 622 and includes at least one coil that contacts the interior surface 15 of the aneurysm 10. In the embodiment shown, the loops of the inner anchoring member 640 do not fill the entire internal volume 14 or a substantial portion of the internal volume 14. Instead, the inner anchoring member 640 includes only a single set of loops extending from the cover 622 like a stem. In some embodiments, the anchoring member 640 may be a soft net coil. In other embodiments, the anchoring member 640 may include a large number of loops substantially filing the internal volume 14. The orientation, number, and size of the loops of the inner anchoring member 640 may vary depending on the size and shape of the aneurysm 10.

Alternatively, the inner cover 622 and the inner cover 522 can be implemented with any inner anchoring members as described in this disclosure. Furthermore, though not depicted in FIG. 24, occlusion device 620 may include any of the outer anchoring members as described in this disclosure, including but not limited to, outer anchoring members 250, 360, 450, 460, 482, and 550.

Referring to FIG. 25, in one exemplary embodiment, an occlusion device 720 having an inner anchoring member 740 is shown. The inner anchoring member 740 is configured to anchor the inner cover 722 within the lower portion of an aneurysm 10, at or near the neck portion 16. The inner anchoring member 740 provides a relatively rigid body that supports the inner cover 722 and reduces the likelihood that the inner cover 722 will be displaced from the neck portion 16 by the fluid pressure of the blood in the blood vessel 12.

According to an exemplary embodiment, the inner cover 722 is a double-layer, formed similarly to the inner cover 522, 622. The inner cover 722 has a peripheral portion to contact the interior surface 15 of the aneurysm 10.

According to an exemplary embodiment, the inner anchoring member 740 is similar to inner anchoring member 640 in that it extends from a substantially central portion of the cover 722 like a stem. In this embodiment, unlike inner anchoring member 640, inner anchoring member 740 is a cylindrical stem made from a sheet of mesh material. The cylindrical stem may be enclosed at a distal end of the stem that contacts the interior surface 15 of the aneurysm 10. The mesh material may be wrapped around a set of loops forming a coil or may be self-supporting. The inner anchoring member 740 may include a plurality of folds 742 forming an accordion-type structure that can be contracted when pressed against an interior surface 15 of the aneurysm 10. In some embodiments, the mesh material is a very fine, high density wire mesh. The mesh material may be a combination of nitinol interlaced with a metal and thread. In some embodiments, the top end 744 of the inner anchoring member 740 is covered or closed.

The inner anchoring member 740 of FIG. 25 may be constructed as a unitary structure with the cover 722. For example, the same sheet of mesh can be used to form the cover 722 with an extending portion forming the stem of the inner anchoring member 740. In other embodiments, the cover 722 and the inner anchoring member 740 are separate elements that are coupled, or molded, together.

Though not depicted in FIG. 25, occlusion device 720 may include any of the outer anchoring members as described in this disclosure, including but not limited to, outer anchoring members 250, 360, 450, 460, 482, and 550.

Referring to FIG. 26A-B, in one exemplary embodiment, an inner cover 822 for an occlusion device is shown. In this embodiment, the inner cover is a multi-layered inner cover 822. Inner cover 822 includes a plurality of leaves 824 arranged in an overlapping relationship with each other, and which are movable individually. The leaves 824 are arranged around a central portion of the inner cover 822. In the side view of FIG. 26A, the inner cover 822 is shown in a partially contracted configuration, wherein the leaves are positioned tightly around the central portion. In FIG. 26B, which is a top view showing the inner cover in an expanded configuration, such as when the inner cover 822 is deployed near the neck 16 of the aneurysm 10, the leaves 824 are extended or fanned out, such that they extend out away from the central portion of the inner cover 822. At least a portion of the leaves 824 of inner cover 822 are configured to contact the interior surface 15 of the aneurysm 10 when in the expanded configuration.

The individual leaves 824 of inner cover 822, according to an exemplary embodiment, are made of a mesh material, such as a biocompatible metal or metal alloy, such as platinum, stainless steel, titanium, a titanium-nickel alloy (e.g., nitinol). Leaves 824 of the inner cover 822 may be formed of a relatively dense mesh such as 37 micron mesh formed by a plurality of wires or fibers that are coupled or molded together. The inner cover 822 may be used in combination with an inner anchoring member as described elsewhere herein, including but not limited to the inner anchoring members and central stems described below and shown in FIGS. 27-32.

FIGS. 27-32 each depict an occlusion device having a similar overall structure. For example, each of the embodiments shown therein include an inner cover (922, 1022, 1122, 1222, 1322, 1422, 1522, 1622) and an inner anchoring member (940, 1040, 1140, 1240, 1340, 1440, 1540, 1640), connected by a central stem (930, 1030, 1130, 1230, 1330, 1430, 1530, 1630). In these embodiments, the inner cover and inner anchoring member are discs having a substantially similar diameter. The central stem may be a cylindrical body having a diameter less than the diameter of the inner cover and inner anchoring member. The inner cover, inner anchoring member, and central stem are all constructed of a mesh material, similar to the occlusion devices described above. In some embodiments of FIGS. 27-32, the inner cover is made of a higher density mesh and the inner anchoring member is made of a lower density mesh.

Various arrangements and combinations are shown and described with reference to FIGS. 27-32. It is contemplated that the present design not be limited to the embodiments shown, but that the various features described in FIGS. 27-32 could be used in other combinations and arrangements with one another. Furthermore, any of the embodiments shown in FIGS. 27-32 may also utilize the multi-layer cover 822 shown in FIGS. 26A-26B. The embodiments shown may also incorporate any of the outer anchoring members, including but not limited to, outer anchoring members (250, 360, 450, 460, 482, and 550) described above.

Figure 27:
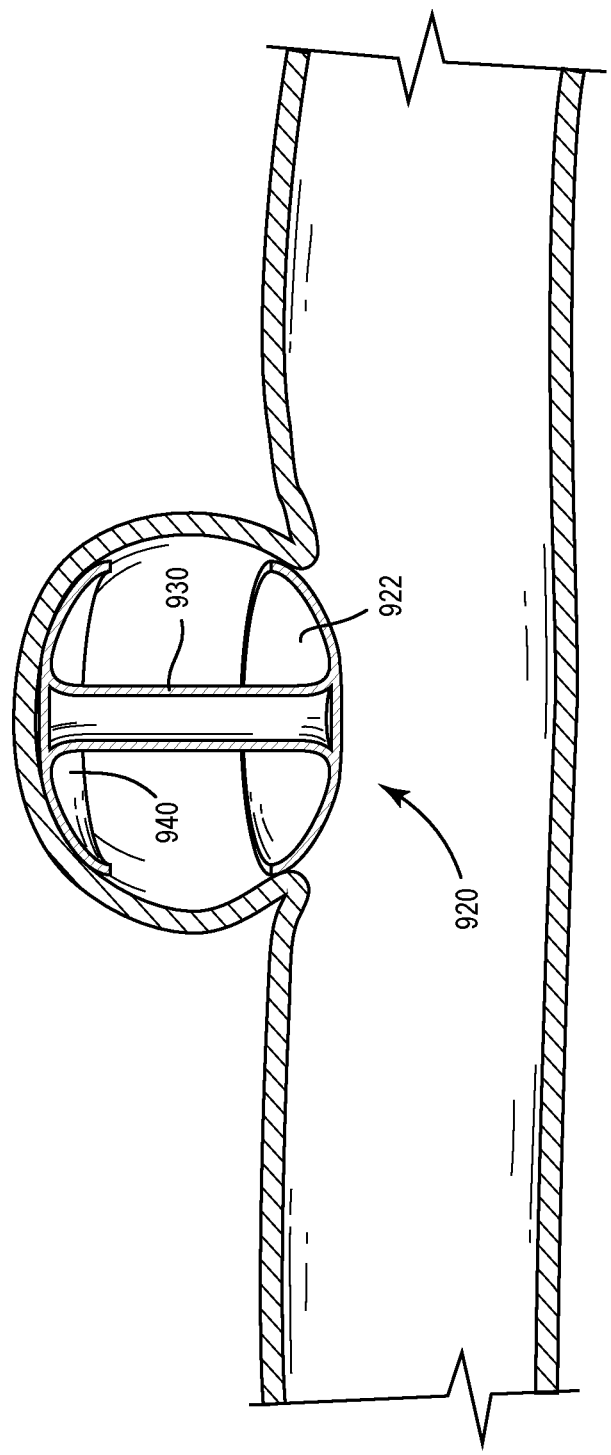
FIG. 27 is a schematic side view of an aneurysm with an endovascular device configured to occlude the aneurysm, according to another exemplary embodiment.

Referring to FIG. 27, in one exemplary embodiment, an occlusion device 920 is shown disposed within the aneurysm 10. Occlusion device 920 has an inner cover 922 and an inner anchoring member 940, connected by a central stem 930. The central stem 930 may be a cylindrical body. The inner cover 922 and inner anchoring member 940 are each generally concave with concavities facing towards the stem 930 and towards one another. The inner cover 922, inner anchoring member 940, and central stem 930 may be constructed separately and coupled together. In other embodiments, the three elements are formed of a single sheet and are unitary. In this embodiment, both the inner cover 922 and the inner anchoring mechanism 940 are constructed of a single-layer disc of the mesh material.

Figure 28:
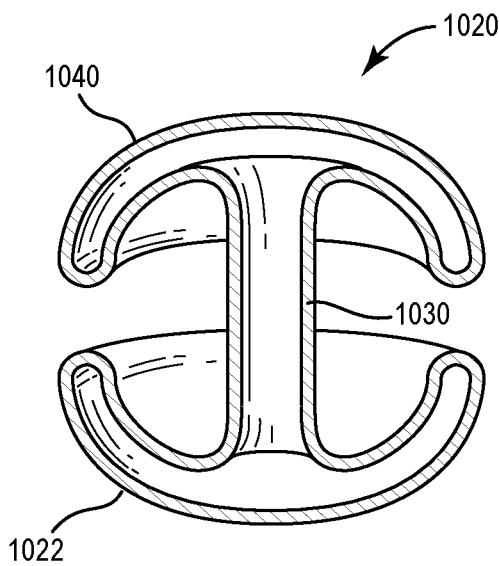
FIG. 28 is a schematic side view of an aneurysm occlusion device, according to an exemplary embodiment.

Referring to FIG. 28, in one exemplary embodiment, an occlusion device 1020 is shown. Occlusion device 1020 has an inner cover 1022 and an inner anchoring member 1040, connected by a central stem 1030. The inner cover 1022 and inner anchoring member 1040 are each generally concave with concavities facing towards the stem 1030 and towards one another. The inner cover 1022, inner anchoring member 1040, and central stem 1030 may be constructed separately and coupled together. In other embodiments, the three elements are formed of a single sheet and are unitary. Occlusion device 1020 of FIG. 28 differs from occlusion device 920 in that both the inner cover 1022 and the inner anchoring mechanism 1040 are constructed of a double-layer of the mesh material, which may be formed in a similar fashion to inner cover 522, 622, or 722 described above.

Figure 29:
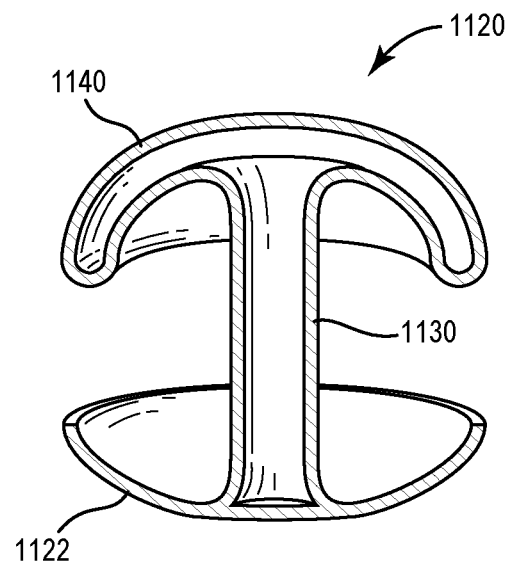
FIG. 29 is a schematic side view of an aneurysm occlusion device, according to an exemplary embodiment.

Referring to FIG. 29, in one exemplary embodiment, an occlusion device 1120 is shown. Occlusion device 1120 has an inner cover 1122 and an inner anchoring member 1140, connected by a central stem 1130. The inner cover 1122 and inner anchoring member 1140 are each generally concave with concavities facing towards the stem 1130 and towards one another. The inner cover 1122, inner anchoring member 1140, and central stem 1130 may be constructed separately and coupled together. In other embodiments, the three elements are formed of a single sheet and are unitary. Occlusion device 1120 of FIG. 29 differs from occlusion device 920 in that the inner cover 1122 is constructed of a single layer of mesh material and the inner anchoring mechanism 1140 is constructed of a double-layer of the mesh material, which may be formed in a similar fashion to inner cover 522, 622, or 722 described above.

Figure 30:
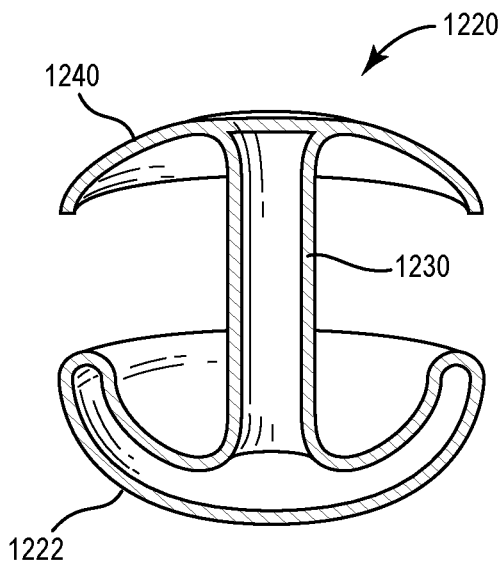
FIG. 30 is a schematic side view of an aneurysm occlusion device, according to an exemplary embodiment.

Referring to FIG. 30, in one exemplary embodiment, an occlusion device 1220 is shown. Occlusion device 1220 has an inner cover 1222 and an inner anchoring member 1240, connected by a central stem 1230. The inner cover 1222 and inner anchoring member 1240 are each generally concave with concavities facing towards the stem 1230 and towards one another. The inner cover 1222, inner anchoring member 1240, and central stem 1230 may be constructed separately and coupled together. In other embodiments, the three elements are formed of a single sheet and are unitary. Occlusion device 1220 of FIG. 30 differs from occlusion device 920 in that the inner anchoring mechanism 1240 is constructed of a single layer of mesh material and the inner cover 1222 is constructed of a double-layer of the mesh material, which may be formed in a similar fashion to inner cover 522, 622, or 722 described above.

Figure 31:
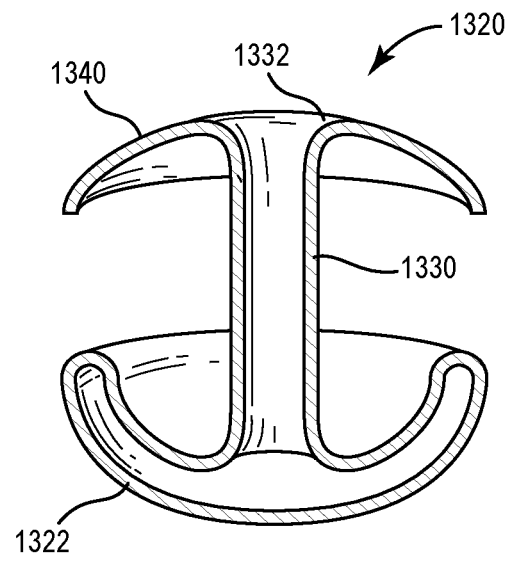
FIG. 31 is a schematic side view of an aneurysm occlusion device, according to an exemplary embodiment.

Referring to FIG. 31, in one exemplary embodiment, an occlusion device 1320 is shown. Occlusion device 1320 has an inner cover 1322 and an inner anchoring member 1340, connected by a central stem 1330. Occlusion device 1320 of FIG. 31 is similar to occlusion device 1220 of FIG. 30 in that the inner anchoring mechanism 1240 is constructed of a single layer of mesh material and the inner cover 1222 is constructed of a double-layer of the mesh material, which may be formed in a similar fashion to inner cover 522, 622, or 722 described above, however, in this embodiment, the inner anchoring mechanism 1340 is single-layer, end portion of the central stem 1330 that is flared out forming an atraumatic end 1332 of the stem 1330. An occlusion device may also include a flared out inner cover in addition to the flared inner anchoring mechanism 1340 shown as part of occlusion device 1320.

Figure 32A:
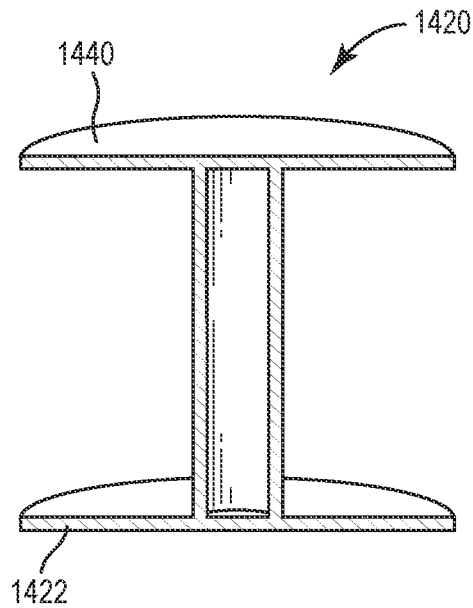
FIG. 32A is a schematic side view of an aneurysm occlusion device, according to an exemplary embodiment.
Figure 32B:
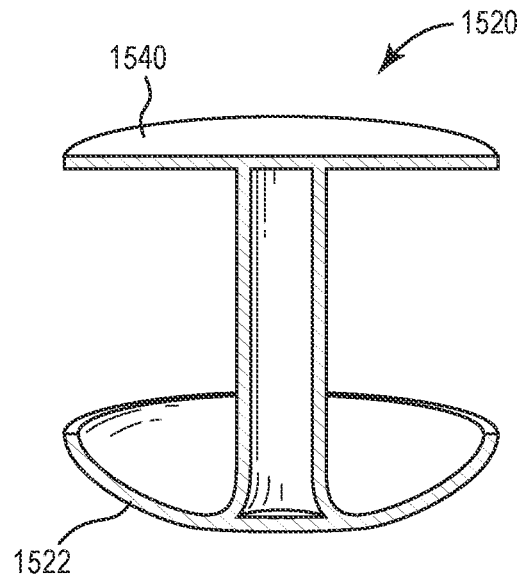
FIG. 32B is a schematic side view of an aneurysm occlusion device, according to an exemplary embodiment.
Figure 32C:
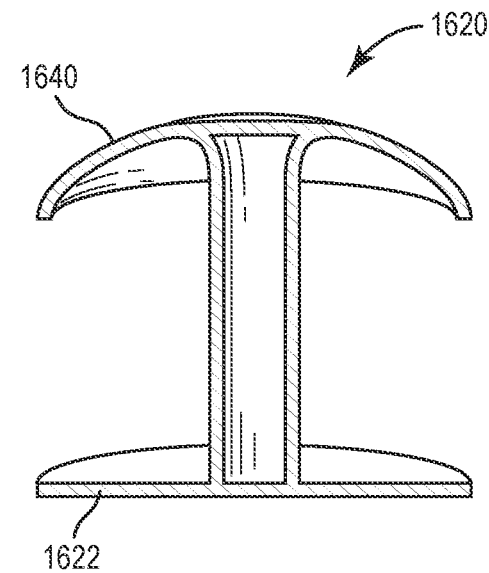
FIG. 32C is a schematic side view of an aneurysm occlusion device, according to an exemplary embodiment.

FIGS. 32A-32C depict other modifications to the occlusion devices, according to exemplary embodiments. Each of these figures depict an occlusion device having an inner cover and an inner anchoring mechanism, connected by a central stem, similar to FIGS. 27-31. In the embodiments of FIGS. 32A-32C it is shown that the inner cover and inner anchoring mechanism may have a variation in shape. For example, the inner cover and/or inner anchoring mechanism may have a flat, uncurved shape. Alternatively, the inner cover and/or inner anchoring mechanism may have an angled or curved shape. In this alternative embodiment, the inner cover and/or inner anchoring mechanism may have a substantially flat central portion with angled or raised edges. FIG. 28, described above, depicts occlusion device 1020 where both the inner cover 1022 and the inner anchoring member 1040 are angled, or curved. FIG. 32A depicts an occlusion device 1420 wherein the inner cover 1422 and the inner anchoring member 1440 are both straight. FIG. 32B depicts an occlusion device 1520 wherein the inner cover 1522 is angled and the inner anchoring member 1540 is straight. FIG. 32C depicts an occlusion device 1620 wherein the inner cover 1622 is straight and the inner anchoring member 1640 is angled.

The construction and arrangement of the elements of the aneurysm occlusion device as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited herein. For example, elements shown as integrally formed may be constructed of multiple parts or elements, the position of elements may be reversed or otherwise varied, and the nature or number of discrete elements or positions may be altered or varied. It should be noted that the elements and/or assemblies of the system may be constructed from any of a wide variety of materials that provide sufficient strength, durability, or biocompatibility. Other substitutions, modifications, changes and omissions may be made in the design, operating conditions and arrangement of the preferred and other exemplary embodiments and medical procedures without departing from the scope of the present invention.

What is claimed is:

1. An apparatus for treating an aneurysm in a blood vessel, the apparatus consisting of:
    a cover disposed on a wire, for covering a neck of an aneurysm,
    wherein the cover is configured to expand from a compressed configuration in a tube to an expanded configuration when advanced out of a distal end of the tube to cover the neck of the aneurysm;
    wherein the cover comprises a sphere of mesh material formed into a hemisphere comprising two layers of mesh that is formed by folding a top portion of the sphere into a bottom portion of the sphere, such that an inner surface of the cover comprises a concavity; and
    wherein the cover is configured to be seated against an interior surface of the aneurysm adjacent the neck of the aneurysm, and to cover the neck of the aneurysm, without contacting the interior surface of the aneurysm at an apex of the aneurysm opposite the neck of the aneurysm, and without contacting any of the blood vessel wall outside of the aneurysm.

2. The apparatus of claim 1, wherein the cover has a cover diameter and is configured to fit into an aneurysm having a neck diameter that is approximately 1 mm less than the cover diameter.

3. The apparatus of claim 1, wherein the cover has a cover diameter and is configured to fit into an aneurysm having a neck diameter that is approximately 2 mm less than the cover diameter.

4. The apparatus of claim 1, wherein the cover has a cover diameter and is configured to fit into an aneurysm having a neck diameter that is approximately 4 mm less than the cover diameter.

5. The apparatus of claim 1, wherein the cover has a cover diameter and is configured to fit into an aneurysm having a neck diameter that is approximately 6 mm less than the cover diameter.

6. The apparatus of claim 1, wherein the cover has a thickness of less than 100 microns.

7. The apparatus of claim 1, wherein the cover is biased toward the expanded configuration.

8. The apparatus of claim 1, wherein the mesh comprises a plurality of wires or fibers.

9. The apparatus of claim 8, wherein the plurality of wires are welded or soldered together.

* * * * *